(12) United States Patent
Raibekas et al.

(10) Patent No.: US 7,619,066 B2
(45) Date of Patent: *Nov. 17, 2009

(54) IL-1RA VARIANTS

(75) Inventors: Andrei Raibekas, Thousand Oaks, CA (US); Bruce Kerwin, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 11/097,453

(22) Filed: Apr. 1, 2005

(65) Prior Publication Data
US 2005/0282752 A1  Dec. 22, 2005

Related U.S. Application Data

(60) Provisional application No. 60/559,161, filed on Apr. 2, 2004, provisional application No. 60/558,879, filed on Apr. 2, 2004, provisional application No. 60/601,229, filed on Aug. 12, 2004, provisional application No. 60/601,216, filed on Aug. 12, 2004.

(51) Int. Cl.
C07K 14/52 (2006.01)
C07K 14/00 (2006.01)
C07K 1/00 (2006.01)
C12N 15/00 (2006.01)

(52) U.S. Cl. .............. 530/351; 530/350; 530/402; 530/412; 435/69.5

(58) Field of Classification Search .............. None
See application file for complete search history.

(56) References Cited

U.S. PATENT DOCUMENTS

| | | | |
|---|---|---|---|
| 4,935,343 A | 6/1990 | Allison et al. | |
| 4,968,607 A | 11/1990 | Dower et al. | |
| 5,081,228 A | 1/1992 | Dower et al. | |
| 5,180,812 A | 1/1993 | Dower et al. | |
| 5,296,592 A | 3/1994 | Dower et al. | |
| 5,319,071 A | 6/1994 | Dower et al. | |
| 5,359,032 A | 10/1994 | Dayer et al. | |
| 5,488,032 A | 1/1996 | Dower et al. | |
| 5,492,888 A | 2/1996 | Dower et al. | |
| 5,510,462 A | 4/1996 | Auron et al. | |
| 5,580,856 A * | 12/1996 | Prestrelski et al. | 514/21 |
| 5,591,457 A | 1/1997 | Bolton | |
| 5,656,627 A | 8/1997 | Bemis et al. | |
| 5,980,954 A | 11/1999 | Bolton | |
| 5,985,657 A | 11/1999 | Auron et al. | |
| 6,020,152 A | 2/2000 | Tedder | |
| 6,323,311 B1 * | 11/2001 | Liu et al. | 530/303 |
| 6,416,753 B1 | 7/2002 | Yuan et al. | |
| 6,511,665 B1 | 1/2003 | Dower et al. | |
| 6,599,873 B1 | 7/2003 | Sommer et al. | |
| 6,660,843 B1 | 12/2003 | Feige et al. | |
| 2005/0159590 A1 * | 7/2005 | Rotman et al. | 530/351 |

FOREIGN PATENT DOCUMENTS

| | | |
|---|---|---|
| EP | 0 502 956 B1 | 4/1997 |
| WO | WO 92/11359 | 7/1992 |
| WO | WO 94/06457 A1 | 3/1994 |
| WO | WO 96/23067 | 8/1996 |
| WO | WO 97/28828 A1 | 8/1997 |
| WO | WO 98/08969 | 3/1998 |
| WO | WO 99/36541 | 7/1999 |
| WO | WO 00/24782 A2 | 5/2000 |
| WO | WO 00/24782 A3 | 5/2000 |
| WO | WO 01/02571 A2 | 1/2001 |
| WO | WO 01/02571 A3 | 1/2001 |
| WO | WO 01/19390 A1 | 3/2001 |
| WO | WO 01/25435 A2 | 4/2001 |
| WO | WO 01/25435 A3 | 4/2001 |
| WO | WO 02/36152 A1 | 5/2002 |
| WO | WO 02/062375 A1 * | 8/2002 |
| WO | WO 2004/022718 A2 | 3/2004 |
| WO | WO 2004/022718 A3 | 3/2004 |

OTHER PUBLICATIONS

Matsushime et al., Blood, 1991, 78:616-623.*
Bottomley et al., "The citrate ion increases the conformational stability of $\alpha_1$-antitrypsin," *Biochem. Biophys. Acta*, 1481:11-17 (2000).
Chen et al., "Strategies to suppress aggregation of recombinant keratinocyte growth factor during liquid formulation development," *J. Pharm. Sci.*, 83:1657-1661 (1994).
Dower et al., "The interleukin-1 receptor," *Immunology Today*, 8(2):46-51 (1987).
Evans et al., "Mapping receptor binding sites in interleukin (IL)-1 receptor antagonist and IL-1β by site-directed mutagenesis," *J. Biol. Chem.*, 270:11477-11483 (1995).

(Continued)

*Primary Examiner*—Gary B Nickol
*Assistant Examiner*—Xiaozhen Xie
(74) *Attorney, Agent, or Firm*—Finnegan, Henderson, Farabow, Garrett & Dunner, L.L.P.

(57) ABSTRACT

The present invention provides for an IL-1ra having reduced aggregation, methods of reducing aggregation of IL-1ra, and kits comprising an IL-1ra having reduced aggregation.

40 Claims, 12 Drawing Sheets

OTHER PUBLICATIONS

Gallivan et al., "Cation-π interactions in structural biology," *Proc. Natl. Acad. Sci. USA*, 96:9459-9464 (1999).

MacLean et al., "Stabilization of proteins by low molecular weight multi-ions," *J. Pharm. Sci.*, 91:2220-2229 (2002).

Schreuder et al., "Refined crystal structure of the interleukin-1 receptor antagonist," *Eur. J. Biochem.*, 227: 838-847 (1995).

Sims et al., "Cloning the interleukin 1 receptor from human T cells," *Proc. Natl. Acad. Sci. USA*, 86:8946-8950 (1989).

Smith at al., "A single amino acid difference between human and monkey interleukin (IL)-1β dictates effective binding to soluble type II IL-1 receptor," *J. Biol. Chem.*, 277:47619-47625 (2002).

van den Burg et al., "Selection of mutations for increased protein stability," *Curr. Opin. Biotech.*, 13:333-337 (2002).

Vigers et al., "X-ray structure of interleukin-1 receptor antagonist at 2.0 Å resolution," *J. Biol. Chem.*, 269:12874-12879 (1994).

Vigers et al., "Crystal structure of the type-I Interleukin-1 receptor complexed with Interleukin-1β," *Nature*, 368:190-194 (1997).

Chang et al., "Development of a stable freeze-dried formulation of recombinant human interleukin-1 receptor antagonist," *Pharmaceutical Research*, 13:243-249(1996).

Chang et al., "Physical factors affecting the storage stability of freeze-dried interleukin-1 receptor antagonist: glass transition and protein conformation," *Archives of Biochemistry and Biophysics*, 331:249-258 (1996).

PCT Notification of Transmittal of the International Search Report and the Written Opinion of the International Searching Authority, or the Declaration, dated May 9, 2006, for Application No. PCT/US2005/011332.

* cited by examiner

Figure 6
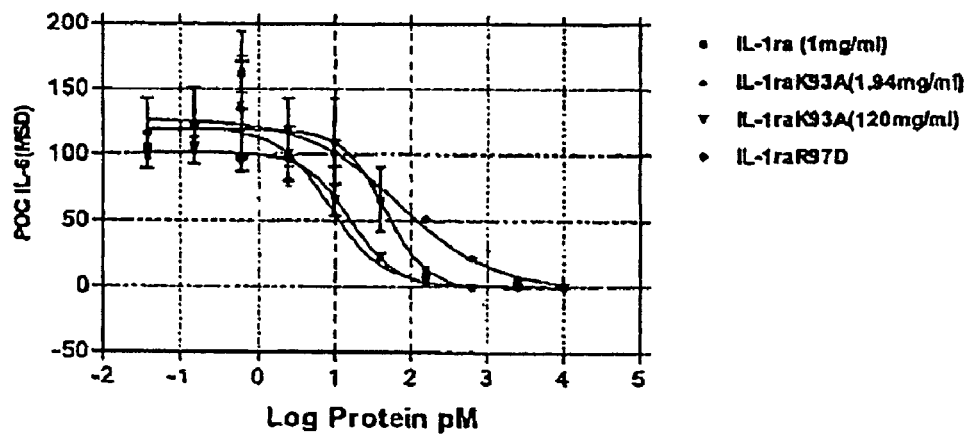
A
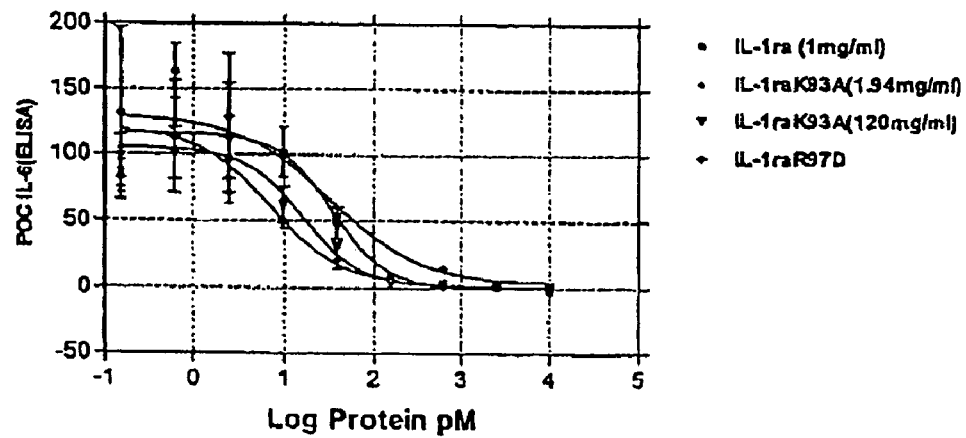
B

SEC of IL-1ra Mutants

FIG. 8

```
           10        20    ↓   30        40        50        60
  GAATTCCGGGCTGCAGTCACAGAATGGAAATCTGCAGAGGCCTCCGCAGTCACCTAATCA
                          M  E  I  C  R  G  L  R  S  H  L  I 70        80        90       100       110       120
  CTCTCCTCCTCTTCCTGTTCCATTCAGAGACGATCTGCCGACCCTCTGGGAGAAAATCCA
   T  L  L  L  F  L  P  H  S  E  T  I  C (R) P  S  G  R  K  S 130       140       150       160       170       180
  GCAAGATGCAAGCCTTCAGAATCTGGGATGTTAACCAGAAGACCTTCTATCTGAGGAACA
   S  K  M  Q  A  F  R  I  W  D  V  N  Q  K  T  F  Y  L  R  N 190       200       210       220       230       240
  ACCAACTAGTTGCTGGATACTTGCAAGGACCAAATGTCAATTTAGAAGAAAAGATAGATG
   N  Q  L  V  A  G  Y  L  Q  G  P  N  V  N  L  E  E  K  I  D 250       260       270       280       290       300
  TGGTACCCATTGAGCCTCATGCTCTGTTCTTGGGAATCCATGGAGGGAAGATGTGCCTGT
   V  V  P  I  E  P  H  A  L  F  L  G  I  H  G  G  K  M  C  L 310       320       330       340       350       360
  CCTGTGTCAAGTCTGGTGATGAGACCAGACTCCAGCTGGAGGCAGTTAACATCACTGACC
   S  C  V  K  S  G  D  E  T  R  L  Q  L  E  A  V  N  I  T  D 370       380       390       400       410       420
  TGAGCGAGAACAGAAAGCAGGACAAGCGCTTCGCCTTCATCCGCTCAGACAGTGGCCCCA
   L  S  E  N  R  K  Q  D  K  R  F  A  F  I  R  S  D  S  G  P 430       440       450       460       470       480
  CCACCAGTTTTGAGTCTGCCGCCTGCCCCGGTTGGTTCCTCTGCACAGCGATGGAAGCTG
   T  T  S  F  E  S  A  A  C  P  G  W  F  L  C  T  A  M  E  A 490       500       510       520       530       540
  ACCAGCCCGTCAGCCTCACCAATATGCCTGACGAAGGCGTCATGGTCACCAAATTCTACT
   D  Q  P  V  S  L  T  N  M  P  D  E  G  V  M  V  T  K  F  Y

550      ↓560       570       580       590       600
  TCCAGGAGGACGAGTAGTACTGCCCAGGCCTGCTGTTCCATTCTTGCATGGCAAGGACTG   SEQ ID NO. 1
   F  Q  E  D  E  *
                                              SEQ ID NO. 2
```

FIG. 9

```
          Ⓔ  P  S  G  R  K  S  S  K  M  Q  A  F  R  I
       Δ
       W  D  V  N  Q  K  T  F  Y  L  R  N  N  Q  L  V  A  G  Ẏ  L
       Q  G  P  N  V  N  L  E  E  K  I  D  V  V  P  I  E  P  H  A
       L  F  L  G  I  H  G  G  K  M  C  L  S  C  V  K  S  G  D  E
       T  R  L  Q  L  E  A  V  N  I  T  D  L  S  E  N  R  K  Q  D
          ✢
       K  R  F  A  F  I  R  S  D  S  G  P  T  T  S  F  E  S  A  A
       C  P  G  W  F  L  C  T  A  H  E  A  D  Q  P  V  S  L  T  N
       M  P  D  E  G  V  M  V  T  K  F  Y  F  Q  E  D  E      SEQ ID NO. 3
```

FIGURE 10

```
  1                                                              cat 4 atgcgaccgtccggccgtaagagctccaaaatgcaggctttccgt
  1 M  R  P  S  G  R  K  S  S  K  M  Q  A  F  R 49 atctgggacgttaaccagaaaaccttctacctgcgcaacaaccag
 16 I  W  D  V  N  Q  K  T  F  Y  L  R  N  N  Q 94 ctggttgctggctacctgcagggtccgaacgttaacctggaagaa
 31 L  V  A  G  Y  L  Q  G  P  N  V  N  L  E  E 139 aaaatcgacgttgtaccgatcgaaccgcacgctctgttcctgggt
 46 K  I  D  V  V  P  I  E  P  H  A  L  F  L  G 184 atccacggtggtaaaatgtgcctgagctgcgtgaaatctggtgac
 61 I  H  G  G  K  M  C  L  S  C  V  K  S  G  D 229 gaaactcgtctgcagctggaagcagttaacatcactgacctgagc
 76 E  T  R  L  Q  L  E  A  V  N  I  T  D  L  S 274 gaaaaccgcaaacaggacaaacgtttcgcattcatccgctctgac
 91 E  N  R  K  Q  D  K  R  F  A  F  I  R  S  D 319 agcggcccgaccaccagcttcgaatctgctgcttgcccgggttgg
106 S  G  P  T  T  S  F  E  S  A  A  C  P  G  W 364 ttcctgtgcactgctatggaagctgaccagccggtaagcctgacc
121 F  L  C  T  A  M  E  A  D  Q  P  V  S  L  T 409 aacatgccggacgaaggcgtgatggtaaccaaattctacttccag
136 N  M  P  D  E  G  V  M  V  T  K  F  Y  F  Q 454 gaagacgaataatgggaagctt 465      SEQ ID NO: 4
151 E  D  E  *                     SEQ ID NO: 5
```

FIGURE 11

```
  1 M  R  P  S  G  R  K  S  S  K  M  Q  A  F  R
 16 I  X₁ D  V  N  Q  K  T  F  Y  L  R  N  N  Q
 31 L  V  A  G  X₂ L  Q  G  P  N  V  N  L  E  E
 46 K  I  D  V  V  P  I  E  P  H  A  L  F  L  G
 61 I  H  G  G  K  M  C  L  S  C  V  K  S  G  D
 76 E  T  R  L  Q  L  E  A  V  N  I  T  D  L  S
 91 E  N  R  X₃ Q  D  K  X₄ F  A  F  I  R  S  D
106 S  G  P  T  T  S  F  E  S  A  A  C  P  G  W
121 F  L  C  T  A  M  E  A  D  Q  P  V  S  L  T
136 N  M  P  D  E  G  V  M  V  T  K  F  Y  F  Q
151 E  D  E  *                    SEQ ID NO: 12
```

FIGURE 12

```
  1  MALETICRPSGRKSSKMQAFRIWDVNQKTFYLRNNQLVAGYLQGPNVNLE   50
 51  EKIDVVPIEPHALFLGIHGGKMCLSCVKSGDETRLQLEAVNITDLSENRK  100
101  QDKRFAFIRSDSGPTTSFESAACPGWFLCTAMEADQPVSLTNMPDEGVMV  150
151  TKFYFQEDE  159          SEQ ID NO: 13
```

IL-1RA VARIANTS

This application claims the benefit of U.S. Provisional Application No. 60/559,161, filed Apr. 2, 2004, U.S. Provisional Application No. 60/558,879, filed Apr. 2, 2004, U.S. Provisional Application No. 60/601,229, filed Aug. 12, 2004, and U.S. Provisional Application No. 60/601,216, filed Aug. 12, 2004. U.S. Provisional Application Nos. 60/559,161, 60/558,879, 60/601,229, and 60/601,216 are incorporated by reference herein for any purpose.

FIELD

The present invention relates to interleukin-1 receptor antagonist (IL-1ra) variants. The present invention also relates to methods of reducing aggregation. The present invention also relates to methods of improving drug formulations comprising IL-1ra having reduced aggregation. Finally, the present invention relates to methods of treating diseases using IL-1ra having reduced aggregation.

BACKGROUND

Interleukin-1 alpha (IL-1α), interleukin-1 beta (IL-1β), and interleukin-1 receptor antagonist (IL-1ra) each binds to the type 1 IL-1 receptor (IL-1RI), which is found on the surface of certain cell types. IL-1α and IL-1β have physiological effects on a number of different target cells, including certain cells that are involved in the inflammatory and immune responses. IL-1ra, in contrast, binds to IL-1RI, but does not elicit comparable downstream biological responses. Rather, IL-1ra competitively inhibits IL-1α and IL-1β binding to IL-1RI. Anakinra, an *E. coli*-produced version of IL-1ra, is marketed for treatment of rheumatoid arthritis.

SUMMARY

In certain embodiments, a method of reducing aggregation of an aggregating interleukin-1 receptor antagonist (IL-1ra) is provided. In certain embodiments, a method of improving an aggregating interleukin-1 receptor antagonist (IL-1ra) drug formulation is provided. In certain embodiments, the method comprises replacing Lysine-93 of IL-1ra with an amino acid that does not have a positive charge. In certain embodiments, the method comprises replacing Arginine-97 of IL-1ra with an amino acid that does not have a positive charge. In certain embodiments, the method comprises replacing Lysine-93 of IL-1ra with a first amino that does not have a positive charge and replacing Arginine-97 with a second amino acid that does not have a positive charge, wherein the first amino acid and the second amino acid are the same or different.

In certain embodiments, the method comprises replacing Lysine-93 of IL-1ra with an amino acid that does not have a charge. In certain embodiments, the method comprises replacing Arginine-97 of IL-1ra with an amino acid that does not have a charge. In certain embodiments, the method comprises replacing Lysine-93 of IL-1ra with a first amino that does not have a charge and replacing Arginine-97 with a second amino acid that does not have a charge, wherein the first amino acid and the second amino acid are the same or different.

In certain embodiments, the method comprises replacing Lysine-93 of IL-1ra with a polar amino acid that does not have a charge. In certain embodiments, the method comprises replacing Arginine-97 of IL-1ra with a polar amino acid that does not have a charge. In certain embodiments, the method comprises replacing Lysine-93 of IL-1ra with a first polar amino acid that does not have a charge and replacing Arginine-97 with a second polar amino acid that does not have a charge, wherein the first polar amino acid and the second polar amino acid are the same or different.

In certain embodiments, the method comprises replacing Lysine-93 of IL-1ra with an amino acid selected from alanine, glycine, glutamine, asparagine, serine, threonine, and tyrosine. In certain embodiments, the method comprises replacing Lysine-93 of IL-1ra with an amino acid selected from alanine and glycine. In certain embodiments, the method comprises replacing Arginine-97 of IL-1ra with an amino acid selected from alanine, glycine, glutamine, asparagine, serine, threonine, and tyrosine. In certain embodiments, the method comprises replacing Arginine-97 of IL-1ra with an amino acid selected from alanine and glycine.

In certain embodiments, the method further comprises incubating the IL-1ra having reduced aggregation with at least one accessory molecule. In certain embodiments, at least one accessory molecule is selected from a sugar and a multiple-charge anion. In certain embodiments, the at least one accessory molecule is 1 to 20 mM pyrophosphate. In certain embodiments, the at least one accessory molecule is 1 to 20 mM citrate. In certain embodiments, the at least one accessory molecule is at least one sugar. In certain embodiments, the at least one sugar is glycerol, sucrose, or sorbitol. In certain embodiments, the at least one sugar is at a concentration of from 1 to 3 percent. In certain embodiments, the at least one accessory molecule is selected from a lysine-reactive accessory molecule and an arginine-reactive accessory molecule. In certain embodiments, the at least one accessory molecule is selected from 6-(N-(7-nitrobenz-2-oxa-1,3-diazol-4-yl)amino)hexanoic acid (NBD-X), methyl acetyl phosphate (MAP), and citraconic anhydride.

In certain embodiments, a method of treating a patient having arthritis is provided. In certain embodiments, a method of treating a patient having rheumatoid arthritis is provided. In certain embodiments, a method of treating a patient having osteoarthritis is provided. In certain embodiments, a method of treating a patient having at least one of Crohn's disease, ulcerative colitis, glomerulonephritis, or leukemia is provided. In certain embodiments, a method of treating a patient having an adverse effect of IL-1 is provided. In certain embodiments, the method comprises administering to the patient a therapeutically effective amount of an IL-1ra having reduced aggregation.

In certain embodiments, a kit comprising an IL-1ra having reduced aggregation is provided.

In certain embodiments, the IL-1ra having reduced aggregation is an IL-1ra wherein Lysine-93 is replaced with an amino acid that does not have a positive charge. In certain embodiments, the IL-1ra having reduced aggregation is an IL-1ra wherein Arginine-97 is replaced with an amino acid that does not have a positive charge. In certain embodiments, the IL-1ra having reduced aggregation is an IL-1ra wherein Lysine-93 is replaced with a first amino acid that does not have a positive charge and Arginine-97 is replaced with a second amino acid that does not have a positive charge, wherein the first amino acid that does not have a positive charge and the second amino acid that does not have a positive charge are the same or different.

In certain embodiments, the IL-1ra having reduced aggregation is an IL-1ra wherein Lysine-93 is replaced with an amino acid that does not have a charge. In certain embodiments, the IL-1ra having reduced aggregation is an IL-1ra wherein Arginine-97 is replaced with an amino acid that does not have a charge. In certain embodiments, the IL-1ra having reduced aggregation is an IL-1ra wherein Lysine-93 is replaced with a first amino acid that does not have a charge and Arginine-97 is replaced with a second amino acid that does not have a charge, wherein the first amino acid that does not have a charge and the second amino acid that does not have a charge are the same or different.

In certain embodiments, the IL-1ra having reduced aggregation is an IL-1ra wherein Lysine-93 is replaced with a polar amino acid that does not have a charge. In certain embodiments, the IL-1ra having reduced aggregation is an IL-1ra wherein Arginine-97 is replaced with a polar amino acid that does not have a charge. In certain embodiments, the IL-1ra having reduced aggregation is an IL-1ra wherein Lysine-93 is replaced with a first polar amino acid that does not have a charge and Arginine-97 is replaced with a second polar amino acid that does not have a charge, wherein the first polar amino acid that does not have a charge and the second polar amino acid that does not have a charge are the same or different.

In certain embodiments, the IL-1ra having reduced aggregation is an IL-1ra wherein Lysine-93 of IL-1ra is an amino acid selected from alanine, glycine, glutamine, asparagine, serine, threonine, and tyrosine. In certain embodiments, the IL-1ra having reduced aggregation is an IL-1ra wherein Lysine-93 of IL-1ra is an amino acid selected from alanine and glycine. In certain embodiments, the IL-1ra having reduced aggregation is an IL-1ra wherein Arginine-97 of IL-1ra is an amino acid selected from alanine, glycine, glutamine, asparagine, serine, threonine, and tyrosine. In certain embodiments, the IL-1ra having reduced aggregation is an IL-1ra wherein Arginine-97 of IL-1ra is an amino acid selected from alanine and glycine.

In certain embodiments, a protein having the amino acid sequence shown in FIG. 11 (SEQ ID NO: 12) is provided. In certain embodiments, the protein has the amino acid sequence shown in FIG. 11 (SEQ ID NO: 12) wherein $X_3$ is an amino acid that does not have a positive charge. In certain embodiments, the protein has the amino acid sequence shown in FIG. 11 (SEQ ID NO: 12) wherein $X_4$ is an amino acid that does not have a positive charge. In certain embodiments, the protein has the amino acid sequence shown in FIG. 11 (SEQ ID NO: 12) wherein $X_3$ is a first amino acid that does not have a positive charge and $X_4$ is a second amino acid that does not have a positive charge, wherein the first amino acid that does not have a positive charge and the second amino acid that does not have a positive charge are the same or different.

In certain embodiments, the protein has the amino acid sequence shown in FIG. 11 (SEQ ID NO: 12) wherein $X_3$ is an amino acid that does not have a charge. In certain embodiments, the protein has the amino acid sequence shown in FIG. 11 (SEQ ID NO: 12) wherein $X_4$ is an amino acid that does not have a charge. In certain embodiments, the protein has the amino acid sequence shown in FIG. 11 (SEQ ID NO: 12) wherein $X_3$ is a first amino acid that does not have a charge and $X_4$ is a second amino acid that does not have a charge, wherein the first amino acid and the second amino acid are the same or different.

In certain embodiments, the protein has the amino acid sequence shown in FIG. 11 (SEQ ID NO: 12) wherein $X_3$ is a polar amino acid that does not have a charge. In certain embodiments, the protein has the amino acid sequence shown in FIG. 11 (SEQ ID NO: 12) wherein $X_4$ is a polar amino acid that does not have a charge. In certain embodiments, the protein has the amino acid sequence shown in FIG. 11 (SEQ ID NO: 12) wherein $X_3$ is a first polar amino acid that does not have a charge and $X_4$ is a second polar amino acid that does not have a e charge, wherein the first amino acid and the second amino acid are the same or different.

In certain embodiments, $X_3$ is an amino acid selected from alanine, glycine, glutamine, asparagine, serine, threonine, and tyrosine. In certain embodiments, $X_4$ is an amino acid selected from alanine, glycine, glutamine, asparagine, serine, threonine, and tyrosine. In certain embodiments, $X_3$ is an amino acid selected from alanine and glycine. In certain embodiments, $X_4$ is an amino acid selected from alanine and glycine.

In certain embodiments, a protein produced in E. coli is provided.

BRIEF DESCRIPTION OF THE FIGURES

FIG. 5A shows percentage of control (POC) versus log of the concentration in pM of either IL-1ra wild-type or mutant protein. FIG. 5B shows best-fit values for competition by IL-1ra wild-type or mutant protein using non-linear regression based on a one-site binding competition model.

FIG. 6 shows the data from a chondrocyte cell-based functional assay that measures decreases in IL-6 expression, which can result from blocking the IL-1 receptor, discussed in Example 4. FIG. 6A shows the results of an MSD-based assay. FIG. 6B shows the results of an ELISA-based assay.

FIG. 8 shows the nucleotide sequence (SEQ ID NO: 1) and amino acid sequence (SEQ ID NO: 2) of precursor human IL-1ra, which includes a secretory leader sequence.

FIG. 9 shows the amino acid sequence of human IL-1ra lacking the secretory leader sequence (SEQ ID NO: 3). The dot (●) indicates the lysine at position 93. The plus (+) indicates the arginine at position 97. The locations of tryptophan-16 (Δ) and tyrosine-34 (○) are also indicated.

FIG. 10 shows the nucleotide sequence (SEQ ID NO: 4) and amino acid sequence (SEQ ID NO: 5) of an IL-1ra used to construct the IL-1ra K93A and IL-1ra R97D mutants, discussed in Example 1.

FIG. 11 shows the amino acid sequence of an IL-1ra with variable amino acids at positions 16 ($X_1$), 34 ($X_2$), 93 ($X_3$), and 97 ($X_4$) (SEQ ID NO: 12). The positions of the variable amino acids are numbered according to the convention discussed herein.

FIG. 12 shows the amino acid sequence of an exemplary IL-1ra, referred to as icIL-1ra (SEQ ID NO: 13). SEQ ID NO:

Figure 1:
FIG. 1 shows an exemplary x-ray crystal structure of IL-1ra.

13 has the same sequence as SEQ ID NO: 3, but with an additional 7 amino acids at the N-terminus.

DETAILED DESCRIPTION OF CERTAIN EXEMPLARY EMBODIMENTS

The section headings used herein are for organizational purposes only and are not to be construed as limiting the subject matter described. All references cited in this application are expressly incorporated by reference herein for any purpose.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

In various embodiments, standard techniques may be used for recombinant DNA, oligonucleotide synthesis, tissue culture, transformation and transfection. In various embodiments, enzymatic reactions and purification techniques may be performed according to manufacturer's specifications or as commonly accomplished in the art or as described herein. In various embodiments, techniques and procedures may be generally performed according to conventional methods known in the art and as described in various general and more specific references that are cited and discussed throughout the present specification and/or that are known to one skilled in the art. See e.g., Sambrook et al. Molecular Cloning: A Laboratory Manual (2d ed., Cold Spring Harbor Laboratory Press, Cold Spring Harbor, N.Y. (1989). Unless specific definitions are provided, the nomenclatures utilized in connection with, and the laboratory procedures and techniques of, analytical chemistry, synthetic organic chemistry, and medicinal and pharmaceutical chemistry described herein are those known and commonly used in the art. In various embodiments, standard techniques may be used for chemical syntheses, chemical analyses, pharmaceutical preparation, formulation, delivery, and treatment of patients. In certain embodiments, where an amino acid is "replaced" with another amino acid, that replacement may be done recombinantly, e.g., by mutating the codon in the polynucleotide that encodes the amino acid to the codon that encodes another amino acid. In certain embodiments, mutating the codon may be done by any method known in the art.

DEFINITIONS

As utilized in accordance with the present disclosure, the following terms, unless otherwise indicated, shall be understood to have the following meanings:

The term "isolated polynucleotide" shall mean a polynucleotide of genomic, cDNA, or synthetic origin, or some combination thereof, which (1) is not associated with at least a portion of a polynucleotide in which it is found in nature, or (2) is linked to a polynucleotide to which it is not linked in nature or (3) does not occur in nature.

The term "operably linked" refers to components that are in a relationship permitting them to function in their intended manner. For example, a control sequence "operably linked" to a coding sequence is ligated in such a way that expression of the coding sequence is achieved under conditions compatible with the operation of the control sequences.

The term "control sequence" refers to polynucleotide sequences which may effect the expression and processing of coding sequences to which they are ligated. The nature of such control sequences may differ depending upon the host organism. According to certain embodiments, control sequences for prokaryotes may include promoters, ribosomal binding sites, and transcription termination sequences. According to certain embodiments, control sequences for eukaryotes may include promoters and transcription termination sequence. In certain embodiments, "control sequences" can include leader sequences and/or fusion partner sequences.

The term "polynucleotide" means a polymeric form of nucleotides having naturally occurring and/or modified ribonucleotides and/or deoxyribonucleotides which are linked together by naturally occurring and/or non-naturally occurring linkages. In certain embodiments, a polynucleotide is least 10 bases in length. The term includes single and double stranded forms of DNA/RNA, and DNA/RNA hybrid, or modified forms thereof.

The term "oligonucleotide" includes polymers having naturally occurring and/or modified ribonucleotides and/or deoxyribonucleotides, which are linked together by naturally occurring and/or non-naturally occurring linkages. Oligonucleotides are a subset of polynucleotides and generally comprise about 200 bases or fewer. In certain embodiments, oligonucleotides are about 10 to about 60 bases in length. In certain embodiments, oligonucleotides are 12, 13, 14, 15, 16, 17, 18, 19, 20, or 21 to 40 bases in length. Oligonucleotides may be single stranded or double stranded. Oligonucleotides may be sense or antisense oligonucleotides.

The term "naturally occurring nucleotides" includes deoxyribonucleotides and ribonucleotides. The term "modified nucleotides" includes nucleotides with modified or substituted sugar groups and/or modified or substituted nucleotide base groups and the like. The terms "oligonucleotide linkage" and "polynucleotide linkage" include linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. Nucl. Acids Res. 14:9081 (1986); Stec et al. J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). In certain embodiments, an oligonucleotide or polynucleotide may include a label.

The term "naturally occurring" as applied to an object refers to an object that can be found in nature. For example, a polypeptide or polynucleotide sequence that is present in an organism (including viruses) that can be isolated from a source in nature and which has not been modified by man in the laboratory or otherwise is naturally occurring.

The term "isolated protein" means a protein made by synthetic means or a protein encoded by genomic DNA, cDNA, RNA, or other polynucleotide, which (1) is free of at least some proteins with which it would normally be found; or (2) is essentially free of other proteins from the same source, e.g., from the same species; or (3) is expressed by a cell from a different species; or (4) does not occur in nature. In the polypeptide notation used herein, the left-hand direction is the amino-terminal direction and the right-hand direction is the carboxy-terminal direction, in accordance with standard usage and convention, unless specifically indicated otherwise.

Similarly, unless specifically indicated otherwise, the left-hand end of single-stranded polynucleotide sequences is the 5' end; the left-hand direction of double-stranded polynucleotide sequences is referred to as the 5' direction. The direction of 5' to 3' addition to nascent RNA transcripts is referred to as the transcription direction; sequence regions on the DNA strand that are 5' to the 5' end of the RNA transcript are referred to as "upstream sequences" and are "upstream of the coding region"; sequence regions on the DNA strand that are 3' to the 3' end of the RNA transcript are referred to as "downstream sequences" and are "downstream of the coding region".

As used herein, the terms "label" or "labeled" refer to the presence of a detectable moiety. A detectable moiety may be incorporated during synthesis of a polynucleotide or polypeptide or may be attached, either covalently or non-covalently, after synthesis. Labeling may be, e.g., incorporation of a radiolabeled amino acid, attachment of biotin moieties that can be detected with labeled avidin (e.g., streptavidin containing a fluorescent moiety or enzymatic activity that can be detected by optical or colorimetric methods). In certain embodiments, the label or detectable moiety can be therapeutic. Various methods of labeling polypeptides and/or polynucleotides are known in the art. Examples of labels for polypeptides and/or polynucleotides include, but are not limited to: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent labels, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce the potential for steric hindrance.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids, such as α-, α-disubstituted amino acids, N-alkyl amino acids, lactic acid, and other unconventional amino acids, may also be suitable components for polypeptides of the present invention. Non-limiting exemplary unconventional amino acids include 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids.

A skilled artisan will be able to identify suitable variants of a polypeptide with well-known techniques. In certain embodiments, one skilled in the art may identify suitable regions of a polypeptide that may be changed without destroying activity by targeting regions not believed to be important for activity. In certain embodiments, one can identify residues and portions of a polypeptide that are conserved among similar polypeptides. In certain embodiments, even areas that may be important for biological activity or for structure may be amenable to conservative amino acid substitutions without destroying the biological activity or without adversely affecting the polypeptide structure.

Additionally, in certain embodiments, one skilled in the art can review structure-function studies and identify residues in similar polypeptides that are important for activity or structure. In view of such a comparison, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can analyze the three-dimensional structure and amino acid sequence in relation to known structures in similar polypeptides. Moreover, in certain embodiments, one skilled in the art may generate test variants containing a single amino acid substitution at each desired amino acid residue. In certain embodiments, the variants can then be screened using activity assays known to those skilled in the art. Such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

In certain embodiments, deletions, insertions, and/or substitutions (individually or collectively referred to as "variant(s)") are made within the amino acid sequence of a IL-1ra wild-type protein. As used herein, "IL-1ra wild-type protein" refers to a protein having the amino acid sequence of SEQ ID NO: 3, optionally having an additional methionine residue at its N-terminus, such that the N-terminal sequence is MRPSGR . . . . The therapeutic protein having the generic name "anakinra" falls within this definition of IL-1ra wild-type protein. Anakinra has the sequence of SEQ ID NO: 5, which is identical to SEQ ID NO: 3, but with an N-terminal methionine. In certain embodiments, alterations to the IL-1ra wild-type protein, such as chemical or enzymatic modification, are made after translation or synthesis of the protein. Such altered IL-1ra proteins are individually or collectively referred to as "derivative(s)". The term IL-1ra encompasses IL-1ra wild-type proteins, as well as naturally occurring and non-naturally occurring IL-1ra variants and derivatives that have antagonist activity for the IL-1ra receptor.

In certain embodiments, an "amino acid that does not have a positive charge" is selected from alanine, cysteine, aspartic acid, glutamic acid, phenylalanine, glycine, histidine, isoleucine, leucine, methionine, asparagine, proline, glutamine, serine, threonine, valine, tryptophan, and tyrosine. Amino acids that do not have a positive charge also include, but are not limited to, unconventional amino acids that do not have a positive charge. One skilled in the art can determine whether or not a particular amino acid variant has a positive charge when incorporated into a polypeptide.

In certain embodiments, an "amino acid that does not have a charge" is selected from alanine, cysteine, phenylalanine, glycine, histidine, isoleucine, leucine, methionine, asparagine, proline, glutamine, serine, threonine, valine, tryptophan, and tyrosine. Amino acids that do not have a charge also include, but are not limited to, unconventional amino acids that do not have a charge. One skilled in the art can determine whether or not a particular unconventional amino acid variant has a charge when incorporated into a polypeptide.

In certain embodiments, a "polar amino acid that does not have a charge" is selected from cysteine, glycine, glutamine, asparagine, serine, threonine, and tyrosine. Polar amino acids that do not have a charge also include, but are not limited to, unconventional amino acids that are polar but do not have a charge. One skilled in the art can determine whether or not a particular unconventional amino acid variant is polar and whether it has a charge when incorporated into a polypeptide.

In certain embodiments, a "non-aromatic amino acid" is selected from alanine, arginine, cysteine, aspartic acid, glutamic acid, glycine, histidine, isoleucine, leucine, lysine, methionine, asparagine, proline, glutamine, serine, threonine, and valine. Non-aromatic amino acids also include, but are not limited to, unconventional amino acids that are not aromatic. One skilled in the art can determine whether or not a particular unconventional amino acid variant is aromatic when incorporated into a polypeptide.

The term "cation-pi interaction" refers to a non-covalent interaction between a cationic amino acid and an aromatic amino acid. In certain embodiments, the cationic amino acid may be lysine. In certain embodiments, the cationic amino acid may be arginine. In certain embodiments, the aromatic amino acid may be phenylalanine. In certain embodiments, the aromatic amino acid may be tyrosine. In certain embodiments, the aromatic amino acid may be tryptophan. The cation-pi interaction may be within a single polypeptide (i.e., intramolecular) or the cation-pi interaction maybe between two or more polypeptides (i.e., intermolecular).

Figure 2:
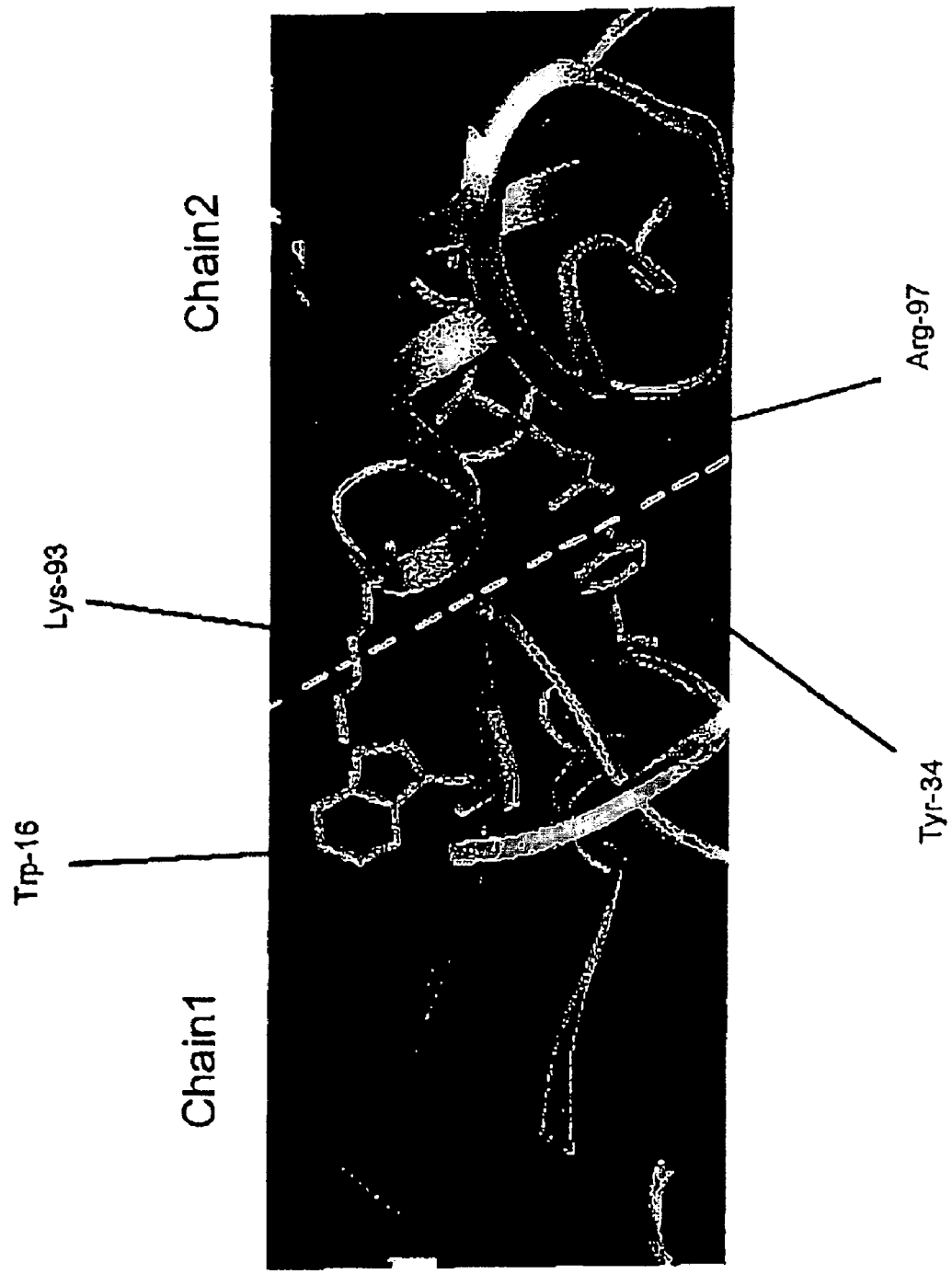
FIG. 2 shows a portion of the interface between the two subunits of the asymmetric IL-1ra dimer in the x-ray crystal structure described for FIG. 1.

In certain embodiments, certain amino acid residues of IL-1ra are involved in a cation-pi interaction. FIG. 1 shows an x-ray crystal structure of IL-1ra. The crystal structure was prepared using a 1 ILR.pdb file and Vector NTI 3D Molecular Viewer (InforMax). IL-1ra crystallized as an asymmetric dimer. See, e.g., Vigers et al., *J. Biol. Chem.*, 269: 12874-12879 (1994). FIG. 2 shows a portion of the crystal structure of FIG. 1. In that crystal structure, lysine-93 on one IL-1ra subunit appears to be involved in a cation-pi interaction with tryptophan-16 on the other IL-1ra subunit. Similarly, arginine-97 on one IL-1ra subunit appears to be involved in a cation-pi interaction with tyrosine-34 on the other IL-1ra subunit.

The term "polypeptide fragment" as used herein refers to a polypeptide that has an amino-terminal and/or a carboxy-terminal deletion. In certain embodiments, fragments are at least 5 to 201 amino acids long. It will be appreciated that in certain embodiments, fragments are at least 5, 6, 8, 10, 14, 20, 50, 70, 80, 90, 100, 110, 125, 150, 170, 175, 176, 177, 180, 185, 190, or 200 amino acids long.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

As used herein, "substantially pure" means an object macromolecular species is the predominant macromolecular species present (i.e., on a molar basis it is more abundant than any other individual macromolecular species in the composition). In certain embodiments, a substantially purified fraction is a composition wherein the object macromolecular species comprises at least about 50 percent (on a weight basis) of all macromolecular species present. In certain embodiments, in a substantially pure composition, the object macromolecular species will comprise more than about 80%, 85%, 90%, 95%, or 99% by weight of all macromolecular species present in the composition. In certain embodiments, the object macromolecular species is purified to essentially homogeneity (i.e., contaminant species cannot be detected in the composition by conventional detection methods). In certain embodiments, the composition consists essentially of a single macromolecular species.

The term patient includes human and animal subjects.

Interleukin-1 receptor antagonist (IL-1ra) is a human protein that acts as an inhibitor of interleukin-1 activity and is a member of the IL-1 family, which also includes IL-1α and IL-1β. A non-exclusive, non-limiting, non-exhaustive list of IL-1 receptor antagonists includes Kineret® (anakinra) (e.g., a protein having the amino acid sequence of SEQ ID NO: 5), IL-1ra wild-type protein (including, but not limited to, a protein having the sequence of SEQ ID NO: 3 or a protein having the sequence of SEQ ID NO: 5), intracellular IL-1ra (icIL-1ra) (including, but not limited to, a protein having the sequence of SEQ ID NO: 13), IL-1ra β (see, e.g., PCT Publication No. WO 99/36541), IL-1ra variants, and IL-1ra derivatives. Certain IL-1ra receptor antagonists, including IL-1ra and variants and derivatives thereof, as well as methods of making and using them, are described, e.g., in U.S. Pat. No. 5,075,222; U.S. Pat. No. 6,599,873 B1; U.S. Pat. No. 5,863,769; U.S. Pat. No. 5,858,355; U.S. Pat. No. 5,739,282; U.S. Pat. No. 5,922,573; U.S. Pat. No. 6,054,559; WO 91/08285; WO 91/17184; WO 91/17249; AU 9173636; WO 92/16221; WO 93/21946; WO 94/06457; WO 94/21275; FR 2706772; WO 94/21235; DE 4219626, WO 94/20517; WO 96/22793; WO 96/12022; WO 97/28828; WO 99/36541; WO 99/51744. An IL-1 receptor antagonist may be glycosylated or non-glycosylated.

Exemplary IL-1ras include, but are not limited to, a polypeptide comprising an amino acid sequence as set forth in SEQ ID NO: 2 and fragments, variants, and derivatives of such a polypeptide that have an antagonist activity for the interleukin-1 receptor; a polypeptide comprising an amino acid sequence as set forth in SEQ ID NO: 3 and fragments, variants, and derivatives of such a polypeptide that have an antagonist activity for the interleukin-1 receptor; a polypeptide comprising an amino acid sequence as set forth in SEQ ID NO: 5 and fragments, variants, and derivatives of such a polypeptide that have an antagonist activity for the interleukin-1 receptor; a polypeptide comprising an amino acid sequence as set forth in SEQ ID NO: 13 and fragments, variants, and derivatives of such a polypeptide that have an antagonist activity for the interleukin-1 receptor.

In certain embodiments, the term IL-1ra includes, but is not limited to, IL-1ra variants that have antagonist activity for the interleukin-1 receptor. In certain embodiments, IL-1ra variants are naturally occurring. In certain embodiments, IL-1ra variants are artificially constructed. Exemplary IL-1ra variants include, but are not limited to, amino acid sequences having one or more amino acid substitutions, deletions, and/or additions as compared to SEQ ID NO: 2, SEQ ID NO: 3, SEQ ID NO: 5, or SEQ ID NO: 13. In certain embodiments, IL-1ra variants comprise an amino acid sequence that is 95% identical to the amino acid sequence of SEQ ID NO: 3. In certain embodiments, IL-1ra variants comprise an amino acid sequence that is 90% identical to the amino acid sequence of SEQ ID NO: 3. In certain embodiments, IL-1ra variants comprise an amino acid sequence that is 85% identical to the amino acid sequence of SEQ ID NO: 3. In certain embodiments, IL-1ra variants comprise an amino acid sequence that is 75% identical to the amino acid sequence of SEQ ID NO: 3.

In certain embodiments, the term IL-1ra includes, but is not limited to, IL-1ra fragments that have antagonist activity for the interleukin-1 receptor. In certain embodiments, IL-1ra fragments are naturally occurring. In certain embodiments, IL-1ra fragments are artificially constructed. Exemplary IL-1ra fragments include, but are not limited to, fragments of the sequence set forth in SEQ ID NO: 2, SEQ ID NO: 3, SEQ ID NO: 5, or SEQ ID NO: 13. IL-1ra fragments are a subset of IL-1ra variants..

In certain embodiments, the term IL-1ra includes, but is not limited to, IL-1ra derivatives that have antagonist activity for the interleukin-1 receptor. In certain embodiments, IL-1ra derivatives are naturally occurring. In certain embodiments, IL-1ra derivatives are artificially constructed. Exemplary IL-1ra derivatives include, but are not limited to, chemically or enzymatically modified forms of the sequence set forth in SEQ ID NO: 2, SEQ ID NO: 3, SEQ ID NO: 5, or SEQ ID NO: 13. Exemplary IL-1ra derivatives also include, but are not limited to, chemically or enzymatically modified forms of variants of the sequence set forth in SEQ ID NO: 2, SEQ ID NO: 3, SEQ ID NO: 5, or SEQ ID NO: 13.

In certain embodiments, the term IL-1ra includes, but is not limited to, an IL-1ra having a secretory leader sequence. In certain embodiments, IL-1ra having a secretory leader sequence is referred to as "precursor IL-1ra." An exemplary precursor IL-1ra amino acid sequence is set forth in SEQ ID NO: 2. The term "precursor IL-1ra" includes fragments, variants, and derivatives of SEQ ID NO: 2 that are capable of being secreted and processed into a form having antagonist activity for the interleukin-1 receptor.

The term IL-1ra includes both aggregating IL-1ra and IL-1ra having reduced aggregation. Aggregating IL-1ra proteins have a lysine at position 93 and an arginine at position 97, but not all IL-1ra proteins with a lysine at position 93 and an arginine at position 97 are aggregating IL-1ras. "Aggregating IL-1ra" includes IL-1ra wild-type, variant, and derivative proteins that aggregate at 39° C. according to the following assay. A solution of 100 mg/ml of the subject IL-1ra is incubated at 39° C. in 10 mM phosphate, 140 mM NaCl, 0.5 mM EDTA, pH 6.5 (PSE). As a reference, a solution of 100 mg/ml of an IL-1ra wild-type protein having the sequence of SEQ ID NO: 5, is incubated in PSE at 39° C. The optical density of each solution is measured at 405 nm after 2 hours of incubation at 39° C. If the subject IL-1ra has an optical density after 2 hours of incubation that is at least 60% of the optical density of the IL-1ra wild-type protein after 2 hours of incubation, then the subject IL-1ra is an aggregating IL-1ra.

"IL-1ra having reduced aggregation" includes IL-1ra variant and derivative proteins that have an optical density that is less than 60% of the optical density of the IL-1ra wild-type protein in the assay described above.

In certain embodiments, the term "an IL-1ra that has antagonist activity for the interleukin-1 receptor" refers to an IL-1ra wild-type, variant, or derivative protein that is at least 50% as active as an IL-1ra wild-type protein having the amino acid sequence of SEQ ID NO: 5, in the IL-1ra signaling complex formation assay described in Example 3. "At least 50% as active" is determined by comparing the EC50 of the subject IL-1ra to the EC50 of IL-1ra wild-type protein.

The term "Arginine-97" refers to the amino acid residue at the 97th position in SEQ ID NO: 3 or the amino acid position in an IL-1ra that corresponds to the amino acid residue at the 97th position in SEQ ID NO: 3. For example, the amino acid that corresponds to arginine-97 of SEQ ID NO: 3 is the arginine at the 98th position of SEQ ID NO: 5. That arginine is still referred to as arginine-97 of IL-1ra. In certain embodiments, Arginine-97 is referred to as "R97," wherein the R is the single-letter code for arginine and 97 refers to its position in SEQ ID NO: 3. In certain embodiments, if R97 is replaced with another amino acid, the mutation may be referred to as R97X, wherein X is the single-letter code for the replacement amino acid. Thus, as a non-limiting example, if R97 is replaced by alanine, the mutation may be referred to as R97A.

The term "Lysine-93" refers to the amino acid residue at the 93rd position in SEQ ID NO: 3 or the amino acid position in an IL-1ra that corresponds to the amino acid residue at the 93rd position in SEQ ID NO: 3. For example, the amino acid that corresponds to lysine-93 of SEQ ID NO: 3 is the lysine at the 94th position of SEQ ID NO: 5. That lysine is still referred to as lysine-93 of IL-1ra. In certain embodiments, Lysine-93 is referred to as "K93," wherein the K is the single-letter code for lysine and 93 refers to its position in SEQ ID NO: 3. In certain embodiments, if K93 is replaced with another amino acid, the mutation may be referred to as K93X, wherein X is the single-letter code for the replacement amino acid. Thus, as a non-limiting example, if K93 is replaced by alanine, the mutation may be referred to as K93A.

The term "Tryptophan-16" refers to the amino acid residue at the 16th position in SEQ ID NO: 3 or the amino acid position in an IL-1ra that corresponds to the amino acid residue at the 16th position in SEQ ID NO: 3. For example, the amino acid that corresponds to tryptophan-16 of SEQ ID NO: 3 is the tryptophan at the 17th position of SEQ ID NO: 5. That tryptophan is still referred to as tryptophan-16 of IL-1ra. In certain embodiments, Tryptophan-16 is referred to as "W16," wherein the W is the single-letter code for tryptophan and 16 refers to its position in SEQ ID NO: 3. In certain embodiments, if W16 is replaced with another amino acid, the mutation may be referred to as W16X, wherein X is the single-letter code for the replacement amino acid. Thus, as a non-limiting example, if W16 is replaced by alanine, the mutation may be referred to as W16A.

The term "Tyrosine-34" refers to the amino acid residue at the 34th position in SEQ ID NO: 3 or the amino acid position in an IL-1ra that corresponds to the amino acid residue at the 34th position in SEQ ID NO: 3. For example, the amino acid that corresponds to tyrosine-34 of SEQ ID NO: 3 is the tyrosine at the 35th position of SEQ ID NO: 5. That tyrosine is still referred to as tyrosine-35 of IL-1ra. In certain embodiments, Tyrosine-34 is referred to as "Y34," wherein the Y is the single-letter code for tyrosine and 34 refers to its position in SEQ ID NO: 3. In certain embodiments, if Y34 is replaced with another amino acid, the mutation may be referred to as Y34X, wherein X is the single-letter code for the replacement amino acid. Thus, as a non-limiting example, if Y34 is replaced by alanine, the mutation may be referred to as Y34A.

In certain embodiments, "reduced aggregation" is defined as (1) aggregation of a polypeptide under condition A that is reduced relative to aggregation of the polypeptide under condition B; and/or (2) aggregation of a polypeptide variant under condition A that is reduced relative to aggregation of the wild-type polypeptide under the same condition A; and/or (3) aggregation of a polypeptide variant under condition A that is reduced relative to aggregation of a different polypeptide variant under the same condition A. As a non-limiting example, relative aggregation may be determined for case (1) as follows. The optical density at 405 nm of a polypeptide under condition A is measured at various times. The optical density at 405 nm of the polypeptide under condition B is then measured at the same various times. The aggregation curve for the object polypeptide under each condition is plotted with optical density on the y-axis and time on the x-axis. If the polypeptide under condition A has a lower optical density at time t than the polypeptide under condition B at the same time t, then the polypeptide under condition A is said to have reduced aggregation relative to the polypeptide under condition B.

Examples of different conditions include, but are not limited to, differences in buffer composition, differences in temperature, differences in polypeptide concentration, the presence and absence of accessory molecules, differences in accessory molecule concentration, etc.

The term "accessory molecule" refers to a molecule that reduces aggregation of one or more polypeptides. In certain embodiments, an accessory molecule reduces aggregation of one or more polypeptides nonspecifically. In certain embodiments, an accessory molecule reduces aggregation by interacting with one or more amino acids of the polypeptide. In certain embodiments, an accessory molecule interacts covalently with one or more amino acids of the polypeptide and is referred to as a "covalent accessory molecule." In certain embodiments, an accessory molecule interacts non-covalently with one or more amino acids of the polypeptide and is referred to as a "non-covalent accessory molecule."

In certain embodiments, the reduction in aggregation of a polypeptide is related to the concentration of the accessory molecule. In certain embodiments, an accessory molecule may substantially eliminate aggregation of a polypeptide.

In certain embodiments, an accessory molecule reduces aggregation of a polypeptide by at least 10%. In certain embodiments, an accessory molecule reduces aggregation of a polypeptide by at least 20%. In certain embodiments, an accessory molecule reduces aggregation of a polypeptide by at least 30%. In certain embodiments, an accessory molecule reduces aggregation of a polypeptide by at least 40%. In certain embodiments, an accessory molecule reduces aggregation of a polypeptide by at least 50%. In certain embodiments, an accessory molecule reduces aggregation of a polypeptide by at least 60%. In certain embodiments, an accessory molecule reduces aggregation of a polypeptide by at least 70%. In certain embodiments, an accessory molecule reduces aggregation of a polypeptide by at least 75%. In certain embodiments, an accessory molecule reduces aggregation of a polypeptide by at least 80%. In certain embodiments, an accessory molecule reduces aggregation of a polypeptide by at least 85%. In certain embodiments, an accessory molecule reduces aggregation of a polypeptide by at least 90%. In certain embodiments, an accessory molecule reduces aggregation of a polypeptide by at least 95%.

In certain embodiments, an accessory molecule reduces the rate of aggregation of a polypeptide. In certain embodiments, the reduction in the rate of aggregation of a polypeptide is dependant on the concentration of the accessory molecule. In certain embodiments, an accessory molecule substantially eliminates aggregation of a polypeptide. In certain embodiments, an accessory molecule reduces the rate of aggregation of a polypeptide by at least 10%. In certain embodiments, an accessory molecule reduces the rate of aggregation of a polypeptide by at least 20%. In certain embodiments, an accessory molecule reduces the rate of aggregation of a polypeptide by at least 30%. In certain embodiments, an accessory molecule reduces the rate of aggregation of a polypeptide by at least 40%. In certain embodiments, an accessory molecule reduces the rate of aggregation of a polypeptide by at least 50%. In certain embodiments, an accessory molecule reduces the rate of aggregation of a polypeptide by at least 60%. In certain embodiments, an accessory molecule reduces the rate of aggregation of a polypeptide by at least 70%. In certain embodiments, an accessory molecule reduces the rate of aggregation of a polypeptide by at least 75%. In certain embodiments, an accessory molecule reduces the rate of aggregation of a polypeptide by at least 80%. In certain embodiments, an accessory molecule reduces the rate of aggregation of a polypeptide by at least 85%. In certain embodiments, an accessory molecule reduces the rate of aggregation of a polypeptide by at least 90%. In certain embodiments, an accessory molecule reduces the rate of aggregation of a polypeptide by at least 95%.

In certain embodiments, an accessory molecule interacts covalently or non-covalently with a polypeptide at one or more amino acid residues. In certain embodiments, an accessory molecule interacts with one or more specific amino acid residues. In certain embodiments, an accessory molecule does not substantially reduce the activity of the polypeptide. In certain embodiments, an accessory molecule does not reduce the activity of the polypeptide by more than 10%. In certain embodiments, accessory molecules to not reduce the activity of the polypeptide by more than 20%. In certain embodiments, an accessory molecule does not reduce the activity of the polypeptide by more than 30%. In certain embodiments, an accessory molecule does not reduce the activity of the polypeptide by more than 50%. In certain embodiments, an accessory molecule does not reduce the activity of the polypeptide by more than 75%.

In certain embodiments, an accessory molecule removes a charge present at an amino acid residue. In certain embodiments, an accessory molecule removes a charge by covalently modifying the amino acid residue. In certain embodiments, an accessory molecule removes a charge by non-covalently interacting with the amino acid residue, thereby "masking" the charge.

Exemplary covalent accessory molecules include, but are not limited to, 6-(N-(7-nitrobenz-2-oxa-1,3-diazol-4-yl)amino)hexanoic acid (NBD-X), methyl acetyl phosphate (MAP), and citraconic anhydride.

Exemplary non-covalent accessory molecules include, but are not limited to, sugars, single-charge anions, and multiple-charge anions. Exemplary sugars that may be accessory molecules include, but are not limited to, glycerol, sucrose, mannitol, and 'sorbitol. Exemplary single-charge anions that may be accessory molecules include, but are not limited to, phosphate and chloride. Exemplary multiple-charge anions that may be accessory molecules include, but are not limited to, pyrophosphate and citrate.

The term "arginine-reactive accessory molecule" refers to an accessory molecule that specifically interacts with arginine residues. In certain embodiments, an arginine-reactive accessory molecule interacts solely with arginine. In certain embodiments, an arginine-reactive accessory molecule interacts with arginine in addition to other amino acids. In certain embodiments, an arginine-reactive accessory molecule interacts covalently with arginine. In certain embodiments, an arginine-reactive accessory molecule interacts non-covalently with arginine. In certain embodiments, an arginine-reactive accessory molecule does not substantially reduce the activity of the polypeptide that contains the arginine.

The term "lysine-reactive accessory molecule" refers to an accessory molecule that specifically interacts with lysine residues. In certain embodiments, an lysine-reactive accessory molecule interacts solely with lysine. In certain embodiments, an lysine-reactive accessory molecule interacts with lysine in addition to other amino acids. In certain embodiments, an lysine-reactive accessory molecule interacts covalently with lysine. In certain embodiments, an lysine-reactive accessory molecule interacts non-covalently with lysine. In certain embodiments, an lysine-reactive accessory molecule does not substantially reduce the activity of the polypeptide that contains the lysine.

The term "multiple-charge anions" refers to molecules that comprise more than one negative charge at pH 6.5 and 25° C. In certain embodiments, multiple-charge anions have on average more than one, but less than two, negative charges at pH 6.5 and 25° C. In certain embodiments, multiple-charge anions have on average two or more negative charges at pH 6.5 and 25° C. In certain embodiments, multiple-charge anions have on average between two and four negative charges at pH 6.5 and 25° C. In various embodiments, one skilled in the art can determine whether a particular anion is a multiple-charge anion at pH 6.5 and 25° C., e.g., from the published pKa values for the anion. The term "single-charge anion" refers to an anion that has on average one, or less than one, negative charge at pH 6.5 and 25° C. In various embodiments, one skilled in the art can determine whether a particular anion is a single-charge anion at pH 6.5 and 25° C., e.g., from the published pKa values for the anion.

The term "sugar" refers to a carbohydrate. Exemplary sugars include, but are not limited to, monosaccharides, disaccharides, and trisaccharides. Non-limiting exemplary sugars include, but are not limited to, glycerol, sucrose, mannitol, and sorbitol.

A disease or medical condition is considered to be an "interleukin-1 mediated disease" if the spontaneous or experimental disease or medical condition is associated with elevated levels of IL-1 in bodily fluids or tissue and/or if cells or tissues taken from the body produce elevated levels of IL-1 in culture. In certain embodiments, such interleukin-1 mediated diseases are also recognized by one or more of the following two conditions: (1) pathological findings associated with the disease or medical condition can be mimicked experimentally in animals by administration of IL-1 or upregulation of expression of IL-1; and/or (2) a pathology induced in experimental animal models of the disease or medical condition can be inhibited or abolished by treatment with agents that inhibit the action of IL-1. In certain embodiments, one or more of the above conditions are met in an IL-1-mediated disease. In certain embodiments, all of the conditions are met in an IL-1-mediated disease.

Acute and chronic interleukin-1 (IL-1) mediated diseases include, but are not limited to, acute pancreatitis; amyotrophic lateral sclerosis (ALS, or Lou Gehrig's disease); Alzheimer's disease; cachexia/anorexia, including, but not limited to, AIDS-induced cachexia; asthma and other pulmonary diseases; atherosclerosis; autoimmune vasculitis; chronic fatigue syndrome; Clostridium associated illnesses, including, but not limited to, Clostridium-associated diarrhea; coronary conditions and indications, including, but not limited to, congestive heart failure, coronary restenosis, myocardial infarction, myocardial dysfunction (e.g., related to sepsis), and coronary artery bypass graft; cancer, including, but not limited to, leukemias, including, but not limited to, multiple myeloma leukemia and myelogenous (e.g., AML and CML), and tumor metastasis; diabetes (including, but not limited to, insulin-dependent diabetes); endometriosis; fever; fibromyalgia; glomerulonephritis; graft versus host disease and/or transplant rejection; hemohorragic shock; hyperalgesia; inflammatory bowel disease; inflammatory conditions of a joint, including, but not limited to, osteoarthritis, psoriatic arthritis, and rheumatoid arthritis; inflammatory eye disease, including, but not limited to, those associated with, for example, corneal transplant; ischemia, including, but not limited to, cerebral ischemia (including, but not limited to, brain injury as a result of, e.g., trauma, epilepsy, hemorrhage or stroke, each of which may lead to neurodegeneration); Kawasaki's disease; learning impairment; lung diseases (including, but not limited to, acute respiratory distress syndrome, or ARDS); multiple sclerosis; myopathies (e.g., muscle protein metabolism, including, but not limited to, muscle protein metabolism in sepsis); neurotoxicity (including, but not limited to, such condition induced by HIV); osteoporosis; pain, including, but not limited to, cancer-related pain; Parkinson's disease; periodontal disease; pre-term labor; psoriasis; reperfusion injury; septic shock; side effects from radiation therapy; temporal mandibular joint disease; sleep disturbance; uveitis; and inflammatory conditions resulting from, e.g., strain, sprain, cartilage damage, trauma, orthopedic surgery, infection, or other disease processes.

DETAILED DESCRIPTION OF CERTAIN EXEMPLARY EMBODIMENTS

Methods of reducing aggregation of an aggregating IL-1ra are provided. In certain embodiments, the aggregating IL-1ra whose aggregation is to be reduced comprises the amino acid sequence in SEQ ID NO: 2, SEQ ID NO: 3, SEQ ID NO: 5, SEQ ID NO: 12, or SEQ ID NO: 13. In certain embodiments, the aggregating IL-1ra whose aggregation is to be reduced comprises a fragment, variant, or derivative of a polypeptide having the amino acid sequence shown in SEQ ID NO: 2, SEQ ID NO: 3, SEQ ID NO: 5, SEQ ID NO: 12, or SEQ ID NO: 13, where that fragment, variant, or derivative has an antagonist activity for the interleukin-1 receptor.

Aggregation of IL-1ra may result from one or more cation-pi interactions between surface residues of two IL-1ra polypeptides. For example, as shown in FIG. 2, lysine-93 of one IL-1 polypeptide may form a cation-pi interaction with tryptophan-16 of a second IL-1 polypeptide. Similarly, arginine-97 of one polypeptide may form a cation-pi interaction with tyrosine-34 of a second polypeptide. Those interactions may cause two IL-1ra polypeptides to bind to one another. Furthermore, because that binding is asymmetric, meaning that binding does not occur between the same face on both polypeptides, each polypeptide may be able to bind to two IL-1ra polypeptides simultaneously. In fact, if additional asymmetric binding contacts are possible between IL-1ra polypeptides, an IL-1ra polypeptide may be able to bind to more than two IL-1ra polypeptides simultaneously. If each IL-1ra polypeptide is capable of binding to at least two other IL-1ra polypeptides, e.g., through the asymmetric cation-pi interaction shown in FIG. 2, then those interactions may lead to aggregation of IL-1ra in solution.

In certain embodiments, aggregation of an aggregating IL-1ra may be reduced by reducing the positive charge at lysine-93, at arginine-97, or at both lysine-93 and arginine-97. In certain embodiments, if the positive charge at one or both of those positions is sufficiently reduced, the cation-pi interaction may not form, or may be weakened such that it is no longer stable enough to cause aggregation of IL-1ra. In certain embodiments, aggregation of an aggregating IL-1ra may be reduced by replacing tryptophan-16 with a non-aromatic amino acid. In certain embodiments, aggregation of an aggregating IL-1ra may be reduced by replacing tyrosine-34 with a non-aromatic amino acid. In certain embodiments, aggregation of an aggregating IL-1ra may be reduced by replacing tryptophan-16 with a first non-aromatic amino acid and replacing tyrosine-34 with a second non-aromatic amino acid, where the first and second non-aromatic amino acids may be the same or different. In certain embodiments, when tryptophan-16, tyrosine-34, or both tryptophan-16 and tyrosine-34 are replaced with a non-aromatic amino acid, aggregation is reduced by reducing one or more of the cation-pi interactions discussed above.

In certain embodiments, aggregation of an aggregating IL-1ra may be reduced by other mechanisms. The method is not limited by the mechanism of the reduction in aggregation. Any of the described methods of reducing aggregation may occur by the exemplary proposed mechanism discussed above or by any other mechanism that achieves the result described. Molecules that are capable of reducing aggregation of an aggregating IL-1ra are collectively referred to as "accessory molecules," regardless of their mechanism of reducing aggregation and regardless of whether they act covalently or non-covalently.

In certain embodiments, aggregation of an aggregating IL-1ra may be reduced by replacing one or more of lysine-93, arginine-97, tryptophan-16, or tyrosine-34. In certain embodiments, lysine-93, arginine-97, or both lysine-93 and arginine-97 are replaced by amino acids that do not have a positive charge. In certain embodiments, an IL-1ra variant may be soluble when expressed in E. coli. For example, in certain embodiments, an IL-1ra K93A mutant protein is in the soluble fraction of a lysates when expressed in E. coli. In certain embodiments, an IL-1ra variant may be insoluble when expressed in E. coli. For example, in certain embodiments, an IL-1ra R97D mutant protein is localized to inclusion bodies when expressed in E. coli. In certain embodiments, an IL-1ra variant that is expressed in a host cell as an insoluble protein may be refolded into a soluble protein, e.g., by the procedure described in Example 1.

Figure 3:
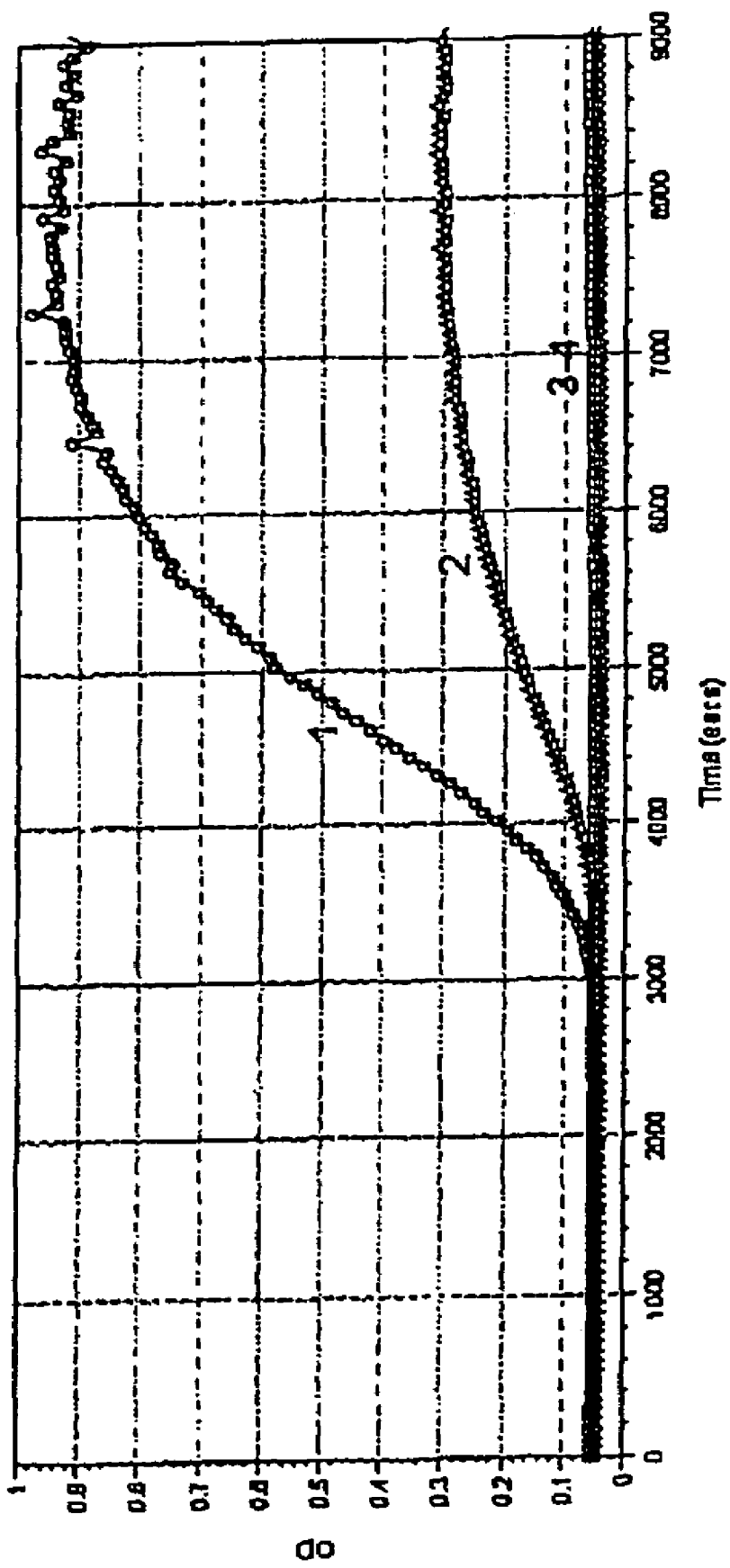
FIG. 3 shows the IL-1ra wild-type and IL-1ra K93A mutant protein aggregation profiles at 40° C. discussed in Example 2. Curve 1 shows the aggregation profile of IL-1ra wild-type protein in PSE. Curve 2 shows the aggregation profile of IL-1ra wild-type protein in CSE. Curve 3 shows the aggregation profile of IL-1ra K93A mutant protein in PSE. Curve 4 shows the aggregation profile of IL-1ra K93A mutant in CSE.

IL-1ra K93A mutant protein may have significantly reduced aggregation relative to IL-1ra wild-type protein. As shown in FIG. 3 and described in Example 2, IL-1ra K93A mutant protein showed little or no aggregation over time in either PSE (line 3) or CSE (line 4) at 40° C., in contrast with IL-1ra wild-type protein, which showed significant aggregation in either PSE (line 1) or CSE (line 2). In that experiment, the extent of aggregation of IL-1ra K93A mutant protein in PSE was less than 10% the extent of aggregation of IL-1ra wild-type protein in PSE at all times after about 100 minutes (6000 seconds). Similarly, although CSE significantly reduced aggregation of IL-1ra wild-type protein (see, e.g., Raibekas and Kerwin, Methods of Reducing Aggregation of IL-1ra, U.S. Provisional Application No. 60/558,879, filed Apr. 2, 2004; Raibekas and Kerwin, Methods of Reducing Aggregation of IL-1ra, U.S. Provisional Application No. 60/601,216, filed Aug. 12, 2004, each of which is incorporated by reference herein for any purpose), the extent of aggregation of IL-1ra wild-type protein in CSE was still about six times the extent of aggregation of IL-1ra K93A mutant protein after about 117 minutes (about 7000 seconds).

Figure 4:
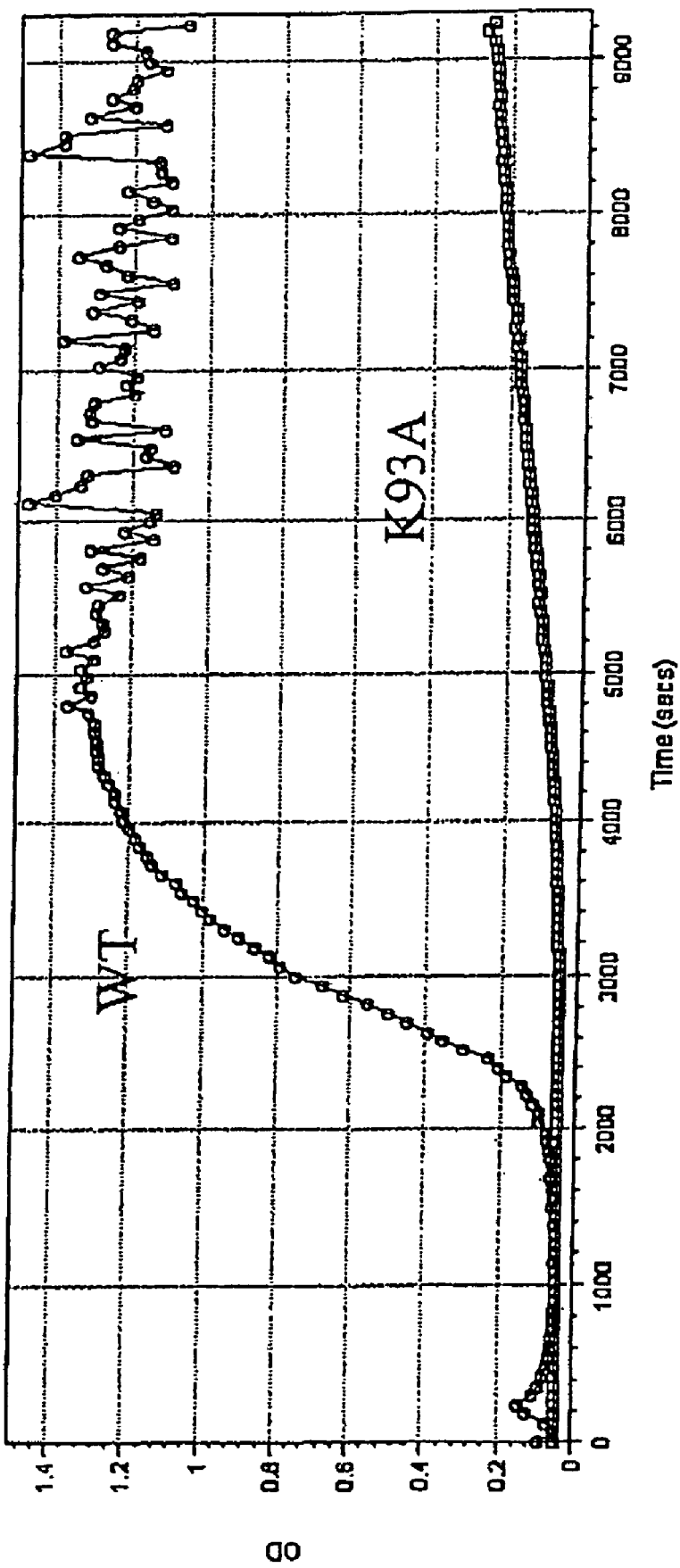
FIG. 4 shows the IL-1ra wild-type protein (WT, 100 mg/ml) and IL-1ra K93A mutant protein (K93A, 100 mg/ml) aggregation profiles at 42° C. in PSE discussed in Example 2.

In certain embodiments, increased temperature may cause increased aggregation of IL-1ra, FIG. 4 shows aggregation of IL-1ra wild-type protein (WT) and IL-1ra K93A mutant protein (K93A) in PSE at 42° C. from the work discussed in Example 2. In contrast to the experiment discussed above (the results of which are shown in FIG. 3), IL-1ra K93A mutant protein showed some aggregation over time at 42° C. in PSE. However, aggregation of IL-1ra wild-type protein was still almost six times greater than aggregation of IL-1ra K93A mutant protein under the same conditions. Thus, even at elevated temperatures, certain IL-1ra variants, including, but not limited to IL-1ra K93A mutant protein, may have reduced aggregation relative to IL-1ra wild-type protein.

In certain embodiments, the activity of an IL-1ra having reduced aggregation in certain activity assays is not substantially reduced relative to IL-1ra wild-type protein in the same activity assay. In certain embodiments, the activity of an IL-1ra having reduced aggregation in which one or more of lysine-93, arginine-97, tryptophan-16, or tyrosine-34 is replaced with a different amino acid, in certain activity assays, is not reduced relative to IL-1ra wild-type protein in the same activity assay. In certain embodiments, the activity of an IL-1ra having reduced aggregation in which lysine-93, arginine-97, or lysine-93 and arginine-97 are replaced with amino acids that do not have a positive charge, in certain activity assays, is not reduced relative to IL-1ra wild-type protein in the same activity assay. In certain embodiments, the activity of an IL-1ra having reduced aggregation in which lysine-93 has been replaced with an amino acid that does not have a positive charge, in certain activity assays, is not reduced relative to IL-1ra wild-type protein in the same activity assay. In certain embodiments, the activity of a IL-1ra having reduced aggregation in which arginine-97 has been replaced with an amino acid that does not have a positive charge, in certain activity assays, is not reduced relative to IL-1ra wild-type protein in the same activity assay.

Figure 5:
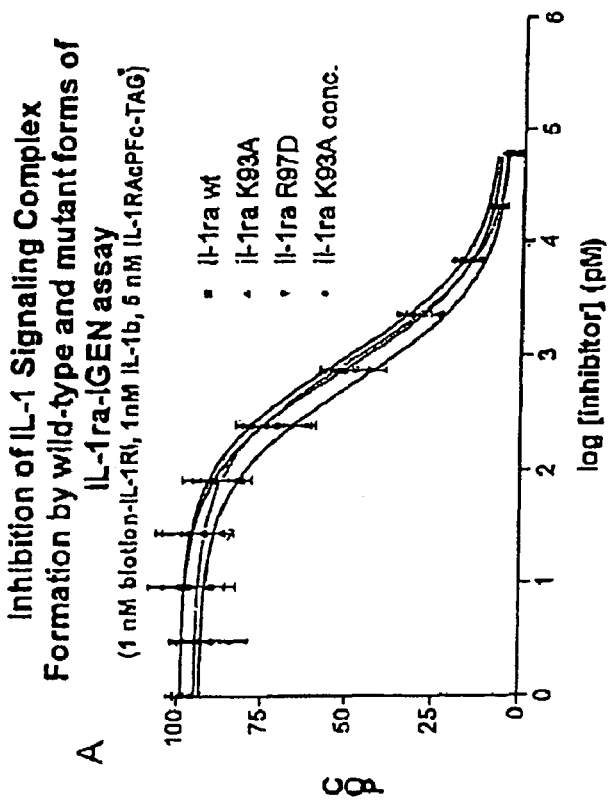
FIG. 5 shows the inhibition of IL-1 signaling complex formation by IL-1ra wild-type protein, IL-1ra K93A mutant protein, and IL-1ra R97D mutant protein discussed in Example 3.

Certain non-limiting exemplary activity assays are shown in FIGS. 5 and 6 and are discussed, e.g., in Examples 3 and 4. FIG. 6 shows the results of an IL-1 signaling complex formation assay discussed in Example 3. In that assay, inhibition of the formation of the IL-1 signaling complex by IL-1ra wild-type protein and two IL-1ra mutant proteins, K93A and R97D, is measured. IL-1ra K93A and R97D mutant proteins were as effective as IL-1ra wild-type protein at inhibiting IL-1 signaling complex formation in the experiment described at Example 3. FIG. 6 shows a cell-based assay discussed in Example 4 that measures the reduction in expression of IL-6 following binding of the IL-1 receptor by IL-1ra wild-type or mutant protein. In that experiment, IL-1ra K93A and R97D mutant proteins were only slightly less effective at reducing IL-1 expression than IL-1ra wild-type protein. All three IL-1ra wild-type and mutant proteins were able to reduce expression of IL-6 to nearly 0 at a concentration of about 3.5 pM in the experiment described at Example 4.

One skilled in the art can determine whether a particular variant has similar or reduced activity relative to IL-1ra wild-type protein in an activity assay using, e.g., the assays described in Examples 3 and 4 and the knowledge in the art. In certain embodiments, the activity of an IL-1ra variant protein is at least 90% that of an IL-1ra wild-type protein at the same concentration. In certain embodiments, the activity of an IL-1ra variant protein is at least 80% that of an IL-1ra wild-type protein at the same concentration. In certain embodiments, the activity of an IL-1ra variant protein is at least 75% that of an IL-1ra wild-type protein at the same concentration. In certain embodiments, the activity of an IL-1ra variant protein is at least 60% that of an IL-1ra wild-type protein at the same concentration. In certain embodiments, the activity of an IL-1ra variant protein is at least 50% that of an IL-1ra wild-type protein at the same concentration.

In certain embodiments, an IL-1ra having reduced aggregation comprises the amino acid sequence of SEQ ID NO: 3 with one or more amino acid substitutions that reduce aggregation but do not reduce the activity by more than 25%, relative to IL-1ra wild-type protein. In certain embodiments, an IL-1ra having reduced aggregation comprises the amino acid sequence of SEQ ID NO: 5 with one or more amino acid substitutions that reduce aggregation but do not reduce the activity by more than 25% relative to IL-1ra wild-type protein.

In certain embodiments, aggregation of an IL-1ra having reduced aggregation may be further reduced by incubating the IL-1ra having reduced aggregation with at least one accessory molecule. In certain embodiments, an accessory molecule reduces the positive charge at lysine-93. In certain embodiments, an accessory molecule reduces the positive charge at arginine-97. In certain embodiments, an accessory molecule reduces the positive charge at both lysine-93 and arginine-97. The positive charge at one or both of those amino acids may be reduced covalently or non-covalently. An accessory molecule postulated to reduce the positive charge at one or both of those amino acids may also reduce aggregation through other mechanisms, or may act by other mechanisms entirely. In certain embodiments, lysine-93 of IL-1ra has been replaced with an amino acid that does not have a positive charge. In certain embodiments, arginine-97 of IL-1ra has been replaced with an amino acid that does not have a positive charge. In certain embodiments, both lysine-93 and arginine-97 have been replaced with amino acids that do not have a positive charge. Where only one of lysine-93 or arginine-97 has been replaced with an amino acid that does not have a positive charge, in certain embodiments, an accessory molecule may further reduce aggregation of the IL-1ra by reducing the charge at whichever of lysine-93 or arginine-97 remains. Where both lysine-93 and arginine-97 have been replaced with amino acids, that do not have a positive charge, an accessory molecule may further reduce aggregation through other mechanisms.

In certain embodiments, incubation of IL-1ra having reduced aggregation with single-charge anionic or multiple-charge anionic molecules may further reduce aggregation of IL-1ra. In certain embodiments, that reduction in aggregation may result from the single-charge anionic or multiple-charge anionic molecule interacting with the positive-charge at lysine-93, at arginine-97, or at both lysine-93 and arginine-97, if either or both of those residues has not been replaced as discussed above.

In certain embodiments, citrate is more effective at reducing aggregation than phosphate (see, e.g., Raibekas and Kerwin, Methods of Reducing Aggregation of IL-1ra, U.S. Provisional Application No. 60/558,879, filed Apr. 2, 2004; Raibekas and Kerwin, Methods of Reducing Aggregation of IL-1ra, U.S. Provisional Application No. 60/601,216, filed Aug. 12, 2004). In certain embodiments, citrate may be more effective at reducing aggregation because it has a greater negative charge than phosphate at pH 6.5. In certain embodiments, certain amounts of negative charge may be more effective than others at reducing aggregation. Furthermore, in certain embodiments, certain configurations of negative charge, e.g., the distance between negative charges on an accessory molecule and how "fixed" those negative charges are in space, may also affect the effectiveness of accessory molecules. Thus, in certain embodiments, the effectiveness of various accessory molecules may be affected by the amount of negative charge, but the amount of negative charge may not always be determinative. In various embodiments, one skilled in the art can select accessory molecules and determine which is appropriate for the specific application contemplated. For example, certain accessory molecules may be more or less effective at certain temperatures. In various embodiments, one skilled in the art can select an accessory molecule that is effective at the particular temperature at which the IL-1ra will be incubated or stored. In certain embodiments, an accessory molecule is selected that is effective at reducing aggregation between about 20° C. and 45° C. In certain embodiments, an accessory molecule is selected that is effective at reducing aggregation between about 25° C. and 45° C. In certain embodiments, an accessory molecule is selected that is effective at reducing aggregation between about 30° C. and 45° C. In certain embodiments, an accessory molecule is selected that is effective at reducing aggregation between about 35° C. and 45° C.

In certain embodiments, altering the concentration of an accessory molecule may affect the reduction in aggregation or the reduction in the rate of aggregation of IL-1ra. As a non-limiting example, in the work discussed in Example 4 and shown in FIG. 3 of Raibekas and Kerwin, Methods of Reducing Aggregation of IL-1ra, U.S. Provisional Application No. 60/558,879, filed Apr. 2, 2004, citrate reduced the rate of aggregation of IL-1ra wild-type protein by almost 90% at 10 mM citrate. In that experiment, citrate further reduced the rate of aggregation to about a 95% reduction at about 20 mM. In contrast, in that experiment, phosphate reduced the rate of aggregation by only about 35% at 20 mM. Citrate has a greater negative charge at pH 6.5 than phosphate, suggesting that, in certain embodiments, the amount of negative charge may affect the effectiveness of certain accessory molecules. In certain embodiments, multiple-charge anions such as citrate and pyrophosphate may further reduce the rate of aggregation of an IL-1ra having reduced aggregation.

In certain embodiments, a sugar may be an accessory molecule. Exemplary sugars that may be accessory molecules include, but are not limited to, sucrose, glycerol, and sorbitol. In certain embodiments, addition of 3% sucrose, glycerol, and/or sorbitol reduces the rate of aggregation of IL-1ra wild-type protein to less than 5 aggregation units (a.u.; 1 a.u. is equal to an increase of 1 milli-optical density unit at 405 nm per minute using a volume of 200 µl and a SpectroMax™ plate-reading spectrophotometer). See, e.g., Example 5 and FIG. 4 of Raibekas and Kerwin, Methods of Reducing Aggregation of IL-1ra, U.S. Provisional Application No. 60/558,879, filed Apr. 2, 2004; and Raibekas and Kerwin, Methods of Reducing Aggregation of IL-1ra, U.S. Provisional Application No. 60/601,216, filed Aug. 12, 2004. In certain embodiments, sugars such as sucrose, glycerol, sorbitol, and mannitol may further reduce the rate of aggregation of an IL-1ra having reduced aggregation.

In various embodiments, one skilled in the art can determine the appropriate concentration of a non-covalent accessory molecule for a particular application by using, e.g., the methods shown in Raibekas and Kerwin, Methods of Reducing Aggregation of IL-1ra, U.S. Provisional Application No. 60/558,879, filed Apr. 2, 2004; Raibekas and Kerwin, Methods of Reducing Aggregation of IL-1ra, U.S. Provisional Application No. 60/601,216, filed Aug. 12, 2004. In certain embodiments, an accessory molecule may be present at a concentration of 1 to 100 mM. In certain embodiments, an accessory molecule may be present at a concentration of 1 to 50 mM. In certain embodiments, an accessory molecule may be present at a concentration of 1 to 20 mM. In certain embodiments, an accessory molecule may be present at a concentration of 10 mM.

In certain embodiments, an accessory molecule may be present at a concentration of between 0 and 10%. In certain embodiments, an accessory molecule may be present at a concentration of between 0 and 5%. In certain embodiments, an accessory molecule may be present at a concentration of 1%, 2%, or 3%.

In certain embodiments, an accessory molecule may reduce aggregation by covalently modifying an aggregating IL-1ra. In certain embodiments, the covalent modification removes a positive charge at lysine-93, at arginine-97, or at both lysine-93 and arginine-97. In certain embodiments, a covalent accessory molecule may reduce aggregation by another mechanism, e.g., by sterically inhibiting formation of one or more cation-pi interactions or other interactions between IL-1ra polypeptides.

Non-limiting exemplary accessory molecules that may covalently modify an IL-1ra include, but are not limited to, NBD-X, citraconic anhydride, and MAP. NBD-X forms a derivative with primary amines. In the work discussed in Example 3 and shown in FIG. 2 of Raibekas and Kerwin, Methods of Reducing Aggregation of IL-1ra, U.S. Provisional Application No. 60/558,879, filed Apr. 2, 2004, incubation of IL-1ra wild-type protein with NBD-X, SE resulted in derivatization of the amino-terminal amine group of the polypeptide and of lysine-93. In certain embodiments, derivatization with NBD-X may remove the positive charge at lysine-93 and may result in reduced aggregation of derivatized IL-1ra. In certain embodiments, MAP acetylates lysine residues and the N-terminal amino groups of polypeptides. In the work discussed in Example 7 and shown in FIGS. 13-15 of Raibekas and Kerwin, Methods of Reducing Aggregation of IL-1ra, U.S. Provisional Application No. 60/558,879, filed Apr. 2, 2004, incubation of IL-1ra with MAP at various times of incubation, resulted in derivatization of the N-terminal amino group of IL-1ra; derivatization of the N-terminal amino group and lysine-6 of IL-1ra; derivatization of the N-terminal amino group, lysine-6, and lysine-93 of IL-1ra; or derivatization of the N-terminal amino group, lysine-6, lysine-93, and lysine-96 of IL-1ra. In certain embodiments, derivatization with MAP may remove the positive charge at lysine-93 and may result in reduced aggregation of derivatized IL-1ra.

In certain embodiments, other amine-reactive molecules may reduce aggregation of IL-1ra by removing one or more positive charges or through another mechanism. In certain embodiments, IL-1ra that has been derivatized with a covalent accessory molecules is at least 90% as active as an IL-1ra wild-type protein that has not been similarly derivatized. In certain embodiments, IL-1ra that has been derivatized with a covalent accessory molecules is at least 80% as active as an IL-1ra wild-type protein that has not been similarly derivatized. In certain embodiments, IL-1ra that has been derivatized with a covalent accessory molecules is at least 75% as active as an IL-1ra wild-type protein that has not been similarly derivatized. In certain embodiments, IL-1ra that has been derivatized with a covalent accessory molecules is at least 50% as active as an IL-1ra wild-type protein that has not been similarly derivatized.

In certain embodiments, kits comprising an IL-1ra having reduced aggregation are provided. In certain embodiments, kits may comprise an IL-1ra in which lysine-93 has been replaced with an amino acid that does not have a positive charge. In certain embodiments, kits may comprise an IL-1ra in which arginine-97 has been replaced with an amino acid that does not have a positive charge. In certain embodiments, kits may comprise an IL-1ra in which lysine-93 has been replaced with a first amino acid that does not have a positive charge and arginine-97 has been replaced with a second amino acid that does not have a positive charge, where the first and second amino acids that do not have a positive charge are the same or different. In certain embodiments, kits may comprise an IL-1ra in which tryptophan-16 has been replaced with a non-aromatic amino acid. In certain embodiments, kits may comprise an IL-1ra in which tyrosine-34 has been replaced with a non-aromatic amino acid. In certain embodiments, a kit comprises IL-1ra K93A mutant protein. In certain embodiments, a kit comprises IL-1ra K93G mutant protein. In certain embodiments, a kit comprises IL-1ra R97D mutant protein. In certain embodiments, a kit comprises IL-1ra K93A, R97D mutant protein, which contains mutations at both lysine-93 and arginine-97. In certain embodiments, a kit comprises IL-1ra R97A mutant protein. In certain embodiments, a kit comprises IL-1ra K93A, R97A mutant protein, which contains mutations at both lysine-93 and arginine-97. In certain embodiments, a kit comprises IL-1ra R97G mutant protein. In certain embodiments, a kit comprises IL-1ra K93A, R97G mutant protein, which contains mutations at both lysine-93 and arginine-97. In certain embodiments, a kit comprises IL-1ra K93G, R97G mutant protein, which contains mutations at both lysine-93 and arginine-97. In certain embodiments, a kit comprises IL-1ra K93G, R97A mutant protein, which contains mutations at both lysine-93 and arginine-97.

In certain embodiments, kits comprising an IL-1ra having reduced aggregation and at least one accessory molecule are provided. In certain embodiments, kits may optionally include instructions for combining the IL-1ra having reduced aggregation and the at least one accessory molecule, if the components are provided separately. In certain embodiments, kits include instructions for using the IL-1ra having reduced aggregation and the at least one accessory molecule. In certain embodiments, the kits may comprise at least one covalent accessory molecule and/or at least one non-covalent accessory molecule. In certain embodiments, when the kit comprises at least one covalent accessory molecule, the kit may comprise instructions for derivatizing the IL-1ra with at least one of the at least one covalent accessory molecule. In certain embodiments, the kit may further comprise instructions for removing remaining unreacted accessory molecule from the derivatized IL-1ra. In certain embodiments, kits comprise an IL-1ra having reduced aggregation that has already been derivatized with at least one covalent accessory molecule. Similarly, in certain embodiments, a kit may comprise an IL-1ra having reduced aggregation that is already in a composition with at least one non-covalent accessory molecule.

In certain embodiments, pharmaceutical compositions are provided comprising a therapeutically effective amount of an IL-1ra having reduced aggregation together with a pharmaceutically acceptable diluent, carrier, solubilizer, emulsifier, preservative and/or adjuvant.

In certain embodiments, acceptable formulation materials are nontoxic to recipients at the dosages and concentrations employed.

In certain embodiments, a pharmaceutical composition may comprise formulation materials for modifying, maintaining and/or preserving, for example, the pH, osmolarity, viscosity, clarity, color, isotonicity, odor, sterility, stability, rate of dissolution or release, adsorption, and/or penetration of the composition. Exemplary formulation materials include, but are not limited to, amino acids (such as glycine, glutamine, asparagine, arginine, and lysine); antimicrobials; antioxidants (such as ascorbic acid, sodium sulfite, and sodium hydrogen-sulfite); buffers (such as borate, bicarbonate, Tris-HCl, citrates, phosphates, and other organic acids); bulking agents (such as mannitol and glycine); chelating agents (such as ethylenediamine tetraacetic acid (EDTA)); complexing agents (such as caffeine, polyvinylpyrrolidone, beta-cyclodextrin, and hydroxypropyl-beta-cyclodextrin); fillers; monosaccharides; disaccharides; and other carbohydrates (such as glucose, mannose, and dextrins); proteins (such as serum albumin, gelatin, and immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid, and hydrogen peroxide); solvents (such as glycerin, propylene glycol, and polyethylene glycol); sugar alcohols (such as mannitol and sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose and sorbitol); tonicity enhancing agents (such as alkali metal halides, such as sodium and potassium chloride, mannitol, sorbitol); delivery vehicles; diluents; excipients and pharmaceutical adjuvants. (See, e.g., Remington's Pharmaceutical Sciences, 18th Edition, A. R. Gennaro, ed., Mack Publishing Company (1990).

In certain embodiments, an IL-1ra and/or one or more additional therapeutic agent are linked to a half-life extending vehicle. Exemplar vehicles include, but are not limited to, the Fc domain, polyethylene glycol, and dextran. Certain exemplary vehicles are described, e.g., in U.S. application Ser. No. 09/428,082 and published PCT Application No. WO 99/25044.

In certain embodiments, an optimal pharmaceutical composition will be determined by one skilled in the art depending upon, for example, the intended route of administration, delivery format, and desired dosage. See, for example, Remington's Pharmaceutical Sciences, supra. In certain embodiments, such compositions may influence the physical state, stability, rate of in vivo release, and rate of in vivo clearance of the IL-1ra.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor.. In certain embodiments, a composition comprising an IL-1ra having reduced aggregation with or without at least one accessory molecule and/or one or more additional therapeutic agents, may be prepared for storage by mixing the selected composition having the desired degree of purity with optional formulation agents (see, e.g., Remington's Pharmaceutical Sciences, supra) in the form of a lyophilized cake or an aqueous solution. Further, in certain embodiments, a composition comprising an IL-1ra having reduced aggregation, with or without at least one accessory molecule and/or one or more additional therapeutic agents, may be formulated as a lyophilizate using appropriate excipients such as sucrose.

In certain embodiments, the pharmaceutical compositions of the invention can be selected for parenteral delivery. In certain embodiments, the compositions may be selected for inhalation or for delivery through the digestive tract, such as orally. The preparation of such pharmaceutically acceptable compositions is within the skill of the art.

In certain embodiments, when parenteral administration is contemplated, a therapeutic composition may be in the form of a pyrogen-free, parenterally acceptable aqueous solution comprising the desired IL-1ra having reduced aggregation, with or without at least one accessory molecule and/or one or more additional therapeutic agents, in a pharmaceutically acceptable vehicle. In certain embodiments, a vehicle for parenteral injection is sterile distilled water in which the IL-1ra having reduced aggregation, with or without at least one accessory molecule and/or one or more additional therapeutic agents, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an IL-1ra having reduced aggregation, with or without at least one accessory molecule and/or one or more additional therapeutic agents, may be formulated as a dry powder for inhalation. In certain embodiments, an inhalation solution comprising an IL-1ra having reduced aggregation, with or without at least one accessory molecule and/or one or more additional therapeutic agents, may be formulated with a propellant for aerosol delivery. In certain embodiments, solutions may be nebulized. Pulmonary administration is further described in PCT application no. PCT/US94/001875, which describes pulmonary delivery of chemically modified proteins.

In certain embodiments, it is contemplated that formulations may be administered orally. In certain embodiments, an IL-1ra having reduced aggregation, with or without at least one accessory molecule and/or one or more additional therapeutic agents, that is administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the IL-1ra and/or any accessory molecules and/or any additional therapeutic agents. In certain embodiments, diluents, flavorings, low melting point waxes, vegetable oils, lubricants, suspending agents, tablet disintegrating agents, and binders may also be employed.

In certain embodiments, a pharmaceutical composition may involve an effective quantity of IL-1ra having reduced aggregation, with or without at least one accessory molecule and/or one or more additional therapeutic agents, in a mixture with non-toxic excipients which are suitable for the manufacture of tablets. In certain embodiments, by dissolving the tablets in sterile water, or another appropriate vehicle, solutions may be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-1ra having reduced aggregation, with or without at least one accessory molecule and/or one or more additional therapeutic agents, in sustained- or controlled-delivery formulations. In certain embodiments, techniques for formulating a variety of other sustained- or controlled-delivery products, such as liposome carriers, bio-erodible microparticles or porous beads and depot injections, are known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (see, e.g., U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions may include liposomes, which can be prepared by any of several methods known in the art. See e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, after the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, kits are provided for producing a single-dose administration unit. In certain embodiments, the kits may each contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an IL-1ra having reduced aggregation, with or without at least one accessory molecule and/or one ore more additional therapeutic agents, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the IL-1ra having reduced aggregation, with or without at least one accessory molecule and/or one or more additional therapeutic agents, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of the IL-1ra having reduced aggregation and/or any accessory molecules and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an IL-1ra having reduced aggregation, with or without at least one accessory molecule and/or one or more additional therapeutic agents, in an ex vivo manner. In such instances, cells, tissues and/or organs that have been removed from the patient are exposed to a pharmaceutical composition comprising an. IL-1ra having reduced aggregation, with or without at least one accessory molecule and/or one or more additional therapeutic agents, after which the cells, tissues and/or organs are subsequently implanted back into the patient.

In certain embodiments, an IL-1ra having reduced aggregation and/or any accessory molecules and/or any additional therapeutic agents can be delivered by implanting certain cells that have been genetically engineered, using methods known in the art, to express and secrete the polypeptides. In certain embodiments, such cells may be animal or human cells, and may be autologous, heterologous; or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved, are provided for illustrative purposes only and are not to be construed as limiting the present invention.

Example 1

Production of IL-1ra Wild-Type and Mutant Proteins

Human recombinant interleukin-1 receptor antagonist (IL-1ra) having the sequence of SEQ ID NO: 5 can be prepared at Amgen manufacturing facilities according to the method discussed in European Patent No. EP 0 502 956 B1, in which the cell recovery step is optional. Alternatively, anakinra, which has the amino acid sequence of SEQ ID NO: 5 may be obtained from Amgen Inc., Thousand Oaks, Calif. Purified human IL-1ra having the amino acid sequence of SEQ ID NO: 5 is referred to as "IL-1ra wild-type protein" in the examples described below.

IL-1ra K93A and IL-1ra R97D mutant proteins may be prepared as follows. The desired mutation may be introduced into a polynucleotide coding sequence for IL-1ra using molecular biology techniques known in the art. The mutant proteins can be prepared by a method known in the art; for example, according to the method discussed in European Patent No. EP 0 502 956 B1, in which the cell recovery step is optional.

The IL-1ra K93A mutant was constructed in two portions, by amplifying the nucleotide sequence of SEQ ID NO: 4, which encodes an IL-1ra having the amino acid sequence of SEQ ID NO: 5, as follows. The polynucleotide sequence of SEQ ID NO: 4 was cloned into the NdeI and HindIII sites of plasmid pAMG21 (ATCC No. 98113; PCT Publication No. WO 01/81377). The 5' end of the coding sequence, up to and including the codon to be mutated, was amplified by PCR using the following primer pair:

```
1209-85
                                        SEQ ID NO: 6
5' CGT ACA GGT TTA CGC AAG AAA ATG G 3'

3214-90
                                        SEQ ID NO: 7
5' CGT TTG TCC TGA GCG CGG TTT TCG CTC AGG 3'
```

Primer 1209-85 hybridizes to vector sequence upstream of the IL-1ra coding sequence. Primer 3214-90 hybridizes to the IL-1ra coding sequence, and changes the codon for lysine at position 93 (AAA) to a codon for alanine (GCT). The 3' end of the coding sequence, from just before the codon to be mutated through the stop codon, was amplified by PCR using the following primer pair:

```
3214-89
                                        SEQ ID NO: 8
5' GAG CGA AAA CCG CGC TCA GGA CAA ACG TTT CGC 3'

1388-00
                                        SEQ ID NO: 9
5' CTA GTT ATT GCT CAG CGG 3'
```

Primer 3214-89 hybridizes to the IL-1ra coding sequence, and also changes the codon for lysine at position 93 (AAA) to a codon for alanine (GCT). Primer 1388-00 hybridizes to vector sequence downstream of the IL-1ra coding sequence.

Each of those PCR amplifications changes the codon encoding lysine at position 93 of IL-1ra to a codon encoding alanine. Each of the resulting PCR products was purified by agarose gel electrophoresis. Aliquots of each purified amplification product were combined, along with the following primer pair, in order to amplify the complete coding sequence for the IL-1ra K93A mutant by PCR:

```
1209-85
                                        SEQ ID NO: 6
5' CGT ACA GGT TTA CGC AAG AAA ATG G 3'

1388-00
                                        SEQ ID NO: 9
5' CTA GTT ATT GCT CAG CGG 3'
```

The full-length IL-1ra coding sequence amplification products were digested with NdeI and HindIII and ligated into pAMG21 (ATCC No. 98113; PCT Publication No. WO 01/81377) cut with NdeI and HindIII.

The presence of the mutation in the IL-1ra coding sequence was confirmed as follows. *E. coli* (Amgen Strain No. 2596, described in U.S. Pat. No. 6,660,843 issued Dec. 9, 2003; PCT Publication No. WO 00/24782; PCT Publication No. WO 01/81377) were transformed with the ligation reaction mixture and plated on nutrient plates containing kanamycin. Growing colonies were picked and tested for expression of IL-1ra K93A mutant protein as follows. Picked colonies were patched onto Luria agar containing 50 ng/ml of homoserine lactone to induce protein expression. The plates were incubated for 17 hours at 37° C. Cells that contain protein expressed as insoluble inclusion bodies appeared opaque, while those that did not contain inclusion bodies appeared translucent. Opaque colonies were scraped from the plates and suspended at about 2% weight to volume in water. The suspension was then mixed with an equal volume of 2× lysis buffer (0.125 M Tris-HCl, pH 7.0, 20% glycerol, 10% SDS, 0.01% bromphenol blue, 10% β-mercaptoethanol) and incubated at 95° C. to 100° C. for five minutes. Twenty μl of lysed cell suspension was then loaded onto a 4-20% SDS PAGE gel. The gel was run at 25 mA (per gel) for 1.3 hours. Gels were then stained with Coomassie Brilliant Blue to visualize the proteins. Colonies that produced a strong band at about 17.3 kDa were selected. Plasmids were isolated from those colonies and were sequenced to confirm the presence of the mutation. A plasmid containing the IL-1ra K93A coding sequence mutation was selected and is referred to as pAMG21-K93A.

The IL-1ra R97D mutant was constructed in two portions, by amplifying the nucleotide sequence of SEQ ID NO: 4, which encodes an IL-1ra having the amino acid sequence of SEQ ID NO: 5, as follows. The polynucleotide sequence of SEQ ID NO: 4 was cloned into the NdeI and HindIII sites of plasmid pAMG21 (ATCC No. 98113; PCT Publication No. WO 01/81377). The 5' end of the coding sequence, up to and including the codon to be, mutated, was amplified by PCR using the following primer pair:

```
1209-85
                                        SEQ ID NO: 6
5' CGT ACA GGT TTA CGC AAG AAA ATG G 3'

3214-88
                                        SEQ ID NO: 10
5' GAA TGC GAG TCG TTT GTC CTG TTT GCG GT 3'
```

Primer 1209-85 hybridizes to vector sequence upstream of the IL-1ra coding sequence. Primer 3214-88 hybridizes to the IL-1ra coding sequence, and changes the codon for phenylalanine at position 98 (TTC) to a codon for leucine (CTC). That mutation is not the desired mutation. However, clones can be selected which have the mutation resulting from primer 3214-87 (discussed below), which creates the desired mutation, instead of the mutation resulting from primer 3214-88. The selection of clones with the desired mutation will be discussed further below. The 3' end of the coding sequence, from just before the codon to be mutated through the stop codon, was amplified by PCR using the following primer pair:

```
3214-87
                                              SEQ ID NO: 11
5' AAA CAG GAC AAA GAC TTC GCA TTC ATC CGC TC 3'

1388-00
                                              SEQ ID NO: 9
5' CTA GTT ATT GCT CAG CGG 3'
```

Primer 3214-87 hybridizes to the IL-1ra coding sequence, and changes the codon for arginine at position 97 (CGT) to a codon for aspartic acid (GAC), which is the desired mutation. Primer 1388-00 hybridizes to vector sequence downstream of the IL-1ra coding sequence.

The PCR amplification in the presence of primers 3214-87 and 1388-00 amplifies the 3' end of IL-1ra and changes the codon encoding arginine at position 97 of IL-1ra to a codon encoding aspartic acid. The PCR amplification in the presence of primers 3214-88 and 1209-85 amplifies the 5' end of IL-1ra and changes the codon encoding phenylalanine at position 98 to a leucine, which is not the desired mutation.. Each of the resulting PCR products was purified by agarose gel electrophoresis. Aliquots of each purified amplification product were combined along with the following primer pair in order to amplify the complete coding sequence for the IL-1ra R97D mutant by PCR:

```
1209-85
                                              SEQ ID NO: 6
5' CGT ACA GGT TTA CGC AAG AAA ATG G 3'

1388-00
                                              SEQ ID NO: 9
5' CTA GTT ATT GCT CAG CGG 3'
```

The PCR amplification will produce 50% full-length IL-1ra coding sequence amplification products that have the desired mutation, R97D, and 50% full-length IL-1ra coding sequence amplification products that have the undesired mutation, F98L.

The full-length IL-1ra coding sequence amplification products were digested with NdeI and HindIII and ligated into pAMG21 (ATCC No. 98113; PCT Publication No. WO 01/81377) cut with NdeI and HindIII. The presence of the R97D mutation in the IL-1ra coding sequence was confirmed as follows. E. coli (Amgen Strain No. 2596, described in U.S. Pat. No. 6,660,843 issued Dec. 9, 2003; PCT Publication No. WO 00/24782; PCT Publication No. WO 01/81377) were transformed with the ligation reaction mixture and plated on nutrient plates containing kanamycin. Growing colonies were picked and tested for expression of IL-1ra mutant protein as follows. Picked colonies were patched onto Luria agar containing 50 ng/ml of homoserine lactone to induce protein expression. The plates were incubated for 17 hours at 37° C. Cells that contain protein expressed as insoluble inclusion bodies appeared opaque, while those that did not contain inclusion bodies appeared translucent. Opaque colonies were scraped from the plates and suspended at about 2% weight to volume in water. The suspension was them mixed with an equal volume of 2× lysis buffer (0.125 M Tris-HCl, pH 7.0, 20% glycerol, 10% SDS, 0.01% bromphenol blue, 10% β-mercaptoethanol) and incubated at 95° C. to 100° C. for five minutes. Twenty μl of lysed cell suspension was then loaded onto a 4-20% SDS PAGE gel. The gel was run at 25 mA (per gel) for 1.3 hours. Gels were then stained with Coomassie Brilliant Blue to visualize the proteins. Colonies that produced a strong band at about 17.3 kDa were selected. Plasmids were isolated from colonies that expressed the 17.3 kDa protein and were sequenced to confirm the presence of the R97D mutation. A plasmid containing the IL-1ra R97D coding sequence mutation was selected and is referred to as pAMG21-R97D.

IL-1ra K93A and IL-1ra R97D proteins were each prepared separately as follows. E. coli (Amgen Strain No. 2596, described in U.S. Pat. No. 6,660,843 issued Dec. 9, 2003; PCT Publication No. WO 00/24782; PCT Publication No. WO 01/81377) were transformed separately with either pAMG21-K93A or pAMG21-R97D. Transformed cells were grown to an optical density at 600 nm ($OD_{600}$) of 1.0 and then stored in 1 ml aliquots in Luria broth (LB) with 17% glycerol at −80° C. For fermentation, the contents of one vial were inoculated into 500 ml of Luria broth and shaken at 37° C. overnight. The 500 ml culture was used to inoculate a fermenter containing 10 L of Luria broth. When the $OD_{600}$ reached 9.5, protein expression was induced by adding 10 ml of 0.5 mg/ml homoserine lactone. Induced E. coli were then grown for an additional 6 hours, reaching a final $OD_{600}$ of 110.

An aliquot of E. coli expressing IL-1ra K93A mutant protein and an aliquot of E. coli expressing IL-1ra R97D mutant protein were each lysed by sonicating (four 1-minute pulses) 100 ml aliquots in a 150 ml beaker. The lysed cells were then separated into soluble and insoluble fractions by centrifuging the lysed cells in a JA-12 rotor for 75 minutes at 12,000 rpm. The soluble and insoluble fractions were then separated by SDS PAGE to determine the localization of each of the mutant proteins. In one experiment, IL-1ra K93A mutant protein was found predominantly in the soluble fraction of an E. coli lysate, while IL-1ra R97D was found predominantly in the insoluble fraction of an E. coli lysate. Accordingly, where a mutant protein is found in an insoluble fraction, it may be refolded and solubilized as described below, or according to other methods, such as certain methods known in the art.

The IL-1ra K93A mutant protein was purified as follows. 152 g cell paste (Amgen strain 2596 transfected with pAMG21-K93A mutant protein, grown and induced as discussed above) was resuspended in 300 ml of cold buffer A (25 mM sodium acetate, pH 5.2, 100 mM NaCl, 1 mM EDTA). 100 ml aliquots of the resuspension were sonicated in a 150 ml beaker by pulsing for 1 minute four times. The sonicated resuspension was centrifuged in a JA-12 rotor at 12,000 rpm for 75 minutes. The IL-1ra K93A mutant protein was in the soluble fraction following centrifugation. The supernatant was removed and the pH of the supernatant adjusted to 5.2 with 1 M acetic acid. The supernatant was then allowed to stand for one hour at room temperature. After standing, the supernatant was centrifuged in a JA-12 rotor at 13,000 rpm for 60 minutes.

The re-centrifuged supernatant was loaded onto an SP-sepharose column (2.5 mm×8 cm), which had been equilibrated with buffer A. The flow rate of the column was set at 60 ml per hour. The column was washed with 2 column volumes of buffer A. A linear gradient of 1 column volume of buffer A and 1 column volume of buffer B (25 mM sodium acetate, pH 5.2, 280 mM NaCl, 1 mM EDTA). After the gradient, the elution from the column was continued with 3.5 column volumes of buffer B. Peak protein fractions were pooled and concentrated from about 142 ml to about 40 ml using an Amicon Ultracel YM10 stirred cell (Millipore). The concentrated protein fractions were then dialyzed against 5 volumes of buffer C (10 mM Histidine, pH 6.0, 50 mM NaCl, 0.1 mM EDTA). Insoluble material was removed by centrifuging the dialyzed solution in a JA-12 rotor at 10,000 rpm for 30 minutes.

The supernatant was then loaded onto a Q-sepharose KL column (2.5 x 6 cm), which had been equilibrated with buffer C. The flow rate of the column was set at 76 ml per hour. The column was washed with 2 column volumes of buffer C. A linear gradient of 100 ml buffer C and 100 ml buffer D (10 mM Histidine, pH 6.0, 200 mM NaCl, 0.1 mM EDTA) was run. Five ml fractions were collected. The protein peak fractions were pooled and concentrated using Amicon Ultracel YM10 stirred cell (Millipore). 562 mg of IL-1ra K93A was purified.

The IL-1ra R97D mutant protein was purified as follows. 85.5 g of cell paste (Amgen strain 2596 transfected with pAMG21-R97D mutant protein, grown and induced as discussed above) was resuspended in 180 ml of cold buffer A (25 mM sodium acetate, pH 5.2, 100 mM NaCl, and 1 mM EDTA). 100 ml aliquots of the resuspension were sonicated in a 150 ml beaker by pulsing for 1 minute four times. The sonicated resuspension was centrifuged in a JA-12 rotor at 12,000 rpm for 75 minutes. The insoluble fraction was washed with 80 ml of water and then centrifuged in a JA-12 rotor at 12,000 rpm for 60 minutes. The insoluble fraction was then washed with 100 ml 1% DOC and then centrifuged in a JA-12 rotor at 12,000 rpm for 60 minutes. The DOC wash was repeated once. The insoluble fraction was washed with 100 ml water and then centrifuged in a JA-12 rotor at 12,000 rpm for 60 minutes. Following the washes and centrifugation, 58 g of insoluble material remained.

The insoluble material was resuspended in 400 ml of 8M urea (192 g urea and 0.96 g of Tris). Cysteine (448 mg) was added to bring the concentration of cysteine to 10 mM and the solution was incubated at room temperature for 10 hours. The solution was then centrifuged in a JA-12 rotor at 12,000 rpm for 75 minutes. Some of the IL-1ra R97D was present in the insoluble fraction.

Cysteine (3.6 g) was then added to 360 ml of the supernatant to bring the cysteine concentration to 74 mM. The solution was incubated at room temperature for 1 hour. The solution was then diluted 10 fold with 1 M urea solution (264 g urea and 24 g Tris were dissolved in 4L water; cysteine (0.988 g) was then added to bring the cysteine concentration to 2 mM). The solution was incubated at 4° C. for 24 hours. The pH of the solution was lowered to 5.2 by addition of 1 M acetic acid. The solution was incubated at 4° C. for 3 days and then centrifuged in a JA10 rotor at 10,000 rpm for 60 minutes. Some of the IL-1ra R97D mutant protein was present in the insoluble fraction.

The supernatant was concentrated from about 4 L to about 1.5 L using an Amicon Ultracel YM10 stirred cell (Millipore). The concentrated supernatant was loaded onto an SP-sepharose column (2.5×8 cm, Amersham) at a flow rate of 100 ml per hour. The column was washed with 2 column volumes of buffer A/urea (25 mM sodium acetate, pH 5.2, 100 mM NaCl, 1 mM EDTA, 1 M urea) and then a linear gradient of 2 column volumes of buffer A/urea and 2 column volumes of buffer B/urea (25 mM sodium acetate, pH 5.2, 280 mM NaCl, 1 mM EDTA, 1 M urea) was run. Proteins were eluted with 3.5 column volumes of buffer B/urea. Five milliliter fractions were collected. Peak fractions were pooled and concentrated from 550 ml to 40 ml using an Amicon Ultracel YM10 stirred cell (Millipore). The concentrated solution was then dialyzed against a buffer containing 25 mM sodium acetate, pH 5.2, 100 mM NaCl, and 5 mM EDTA for 4 hours at 4° C. 352 mg of IL-1ra R97D was purified.

Example 2

Aggregation of IL-1ra Wild-Type Protein and IL-1ra K93A Mutant Protein

Aggregation of each of IL-1ra wild-type protein and IL-1ra K93A mutant protein in both phosphate buffer and citrate buffer was determined at 40° C. as follows. Protein stock solution (200-220 mg/ml protein in 10 mM sodium citrate, 140 mM NaCl, 0.5 mM EDTA, pH 6.5 (CSE)) was dialyzed at 4° C. overnight against either 2×2 L 10 mM phosphate, 140 mM NaCl, 0.5 mM EDTA, pH 6.5 (PSE) or 2×2 L CSE. The dialyzed solution was filtered through a 0.2 μm filter and the protein concentration was adjusted to 100 mg/ml by diluting with the appropriate buffer.

Aggregation of each of IL-1ra wild-type protein or IL-1ra K93A mutant protein in each buffer was measured using a 96-well glass plate (Zissner) and a temperature-controlled plate reading spectrophotometer, SpectraMax Plus (Molecular Devices). The sample size per well was 180 μl. The plates were incubated in the spectrophotometer at 40° C. and the optical density measured at 405 nm every 1 minute. FIG. 3 shows the results of this experiment. The optical density at 405 nm at 40° C. was plotted as a function of time for IL-1ra wild-type protein in PSE (curve 1), IL-1ra wild-type protein in CSE (curve 2), IL-1ra K93A mutant protein in PSE (curve 3), and IL-1ra K93A mutant protein in CSE (curve 4). In this experiment, aggregation of IL-1ra wild-type protein incubated in CSE was reduced relative to aggregation of IL-1ra wild-type protein incubated in PSE. IL-1ra wild-type protein in both CSE and PSE at 40° C. showed significant aggregation over time. In contrast, IL-1ra K93A mutant protein showed little or no aggregation in either PSE or CSE at 40° C. These results suggest that replacing the lysine at position 93 of IL-1ra with an alanine significantly reduces aggregation of IL-1ra in either buffer at 40° C.

IL-1ra wild-type protein and IL-1ra K93A mutant protein aggregation in PSE at 42° C. was determined as described above, except the plates were incubated in the spectrophotometer at 42° C. The results of this experiment are shown in FIG. 4. IL-1ra K93A mutant protein in PSE at 42° C. showed significantly reduced aggregation relative to IL-1ra wild-type protein under the same conditions.

Example 3

Inhibition of IL-1 Signaling Complex Formation by IL-1ra Wild-Type Protein, IL-1ra K93A Mutant Protein, and IL-1ra R97D Mutant Protein IL-1ra wild-type protein inhibits the formation of the IL-1 signaling complex by binding to the type 1 IL-r receptor (IL-1RI) and preventing the recruitment of the IL-1 receptor accessory protein (IL-1RAcP; see, e.g., PCT Publication No. 96/23067; Smith et al., Immunity 18: 87-96 (2002)). A signaling complex formation assay was therefore used to determine whether the IL-1ra mutant proteins, IL-1ra K93A and IL-1ra R97D, are also capable of inhibiting the formation of the IL-1 signaling complex, according to the assay described below. This assay is known in the art for anakinra. See also, e.g., PCT Publication No. WO 2004/022718.

All dilutions described for this assay in Example 3 were done in assay buffer, which contains 0.1% Tween-20 and 1% BSA in PBS. A 4× stock of IL-1RI-coated magnetic beads was prepared by adding 1.04 µl of a 21.2 µM stock of biotinylated human IL-1RI (Amgen Inc.; see, e.g., Vigers et al., Nature, 386: 190-194 (1997); Sims et al., Proc. Natl. Acad. Sci. USA 86: 8946-8950 (1989)) and 55 µl of a 10 mg/ml stock of streptavidin-coated beads (Dynabeads M-280 (Dynal) to 5443.96 µl of assay buffer and incubating the mixture for 30 minutes at room temperature. The 4'3 stock of IL-1RI-coated magnetic beads contained 4 nM biotin-IL-1RI and 100 µg/ml beads. Fifty microliters of the 4× stock of IL-1RI-coated magnetic beads were then dispensed to each well of a 96-well polypropylene microtiter plate.

The test proteins stocks, which included IL-1ra wild-type protein (stock concentration=1 mg/ml), IL-1ra K93A mutant protein (stock concentration=1.94 mg/ml), IL-1ra K93A mutant protein conc. (stock concentration=120 mg/ml), and IL-1ra R97D mutant protein (stock concentration=0.7 mg/ml) were separately serially diluted in assay buffer to concentrations ranging from 240 nM to 4.04 pM. The specific concentrations made were 240 nM, 80 nM, 26.7 nM, 8.89 nM, 2.96 nM, 987.7 pM, 329.2 pM, 109.7 pM, 36.6 pM, 12.2 pM, and 4.1 pM (these concentrations are 4× the final concentrations, which were 60 nM, 20 nM, 2.22 nM, 740.74 pM, 246.91 pM, 82.30 pM, 27.43 pM, 9.14 pM, 3.05 pM, 1.02 pM). Fifty microliters of the test protein 4× stocks were added to separate wells of the 96-well plate containing the coated magnetic beads.

Fifty microliters of 4 nM recombinant mature human IL-1β (Amgen Inc.; see, e.g., Smith et al., J. Biol. Chem., 277: 47619 (2002)) was added to the each of wells (final concentration in the reaction was 1 nM). IL-1RAcP-Fc (Amgen Inc.), which is the IL-1 receptor accessory protein conjugated to Fc of human IgG1, was labeled with N-hydroxysuccinimide ester-activated tris(bipyridine) chelated ruthenium(II) TAG (IGEN International, Inc.) according to the IGEN protocol to make IL-1RAcP-Fc-TAG. Fifty microliters of 20 nM IL-1RAcP-Fc-TAG in assay buffer was added to each well (final concentration in the reaction was 5 nM). A "HI" control reaction containing 50 µl assay buffer in place of an IL-1ra test sample was included in the assay. Also, a "LOW" control reaction containing 100 µl assay buffer in place of both IL-1 and an IL-1ra test sample was included in the assay. The binding reactions were incubated in the dark for 2 hours at room temperature.

The binding reactions were analyzed using an M8 instrument (IGEN International, Inc.). IL-1 RAcP-Fc-TAG binding to IL-1β-bound IL-1RI was measured by detecting the electrochemiluminescence (ECL) signal associated with the IL-1RI-coated beads. The average ECL signal for the "LOW" control wells was subtracted from the ECL values for all other wells. The reduction in signal resulting from competition between IL-1β and each of the test proteins for binding to IL-1RI was calculated as a percentage of the ECL signal for maximum IL-1β binding ("HI" control wells, no test proteins added). The inhibition response curve for each test protein was plotted and the corresponding $IC_{50}$ values (the concentration of test protein that reduces the signal by 50%) were calculated using GraphPad PRISM™ software.

The results of this experiment are shown in FIG. 5. FIG. 5A shows percentage of control (POC) of the ECL signal versus the log of the concentration of IL-1ra wild-type or mutant protein in pM. FIG. 5B shows best-fit values for competition by IL-1ra wild-type and mutant proteins using non-linear regression based on a one-site binding competition model. In this experiment, the IL-1ra K93A and IL-1ra R97D mutant proteins were about as effective as IL-1ra wild-type protein at inhibiting IL-1β binding to IL-1RI in the IL-1 signaling complex formation assay.

Example 4

Reduction of IL-6 Production in Chondrocyte Cells Incubated with IL-1ra Wild-Type protein, IL-1ra K93A Mutant Protein, or IL-1ra R97D Mutant Protein To determine whether the IL-1ra mutant proteins were able to block the IL-1 receptor on the surface of cells, IL-6 expression was measured following incubation of chondrocytes with IL-1ra wild-type protein, IL-1ra K93A mutant protein, or IL-1ra R97D mutant protein, according to the assay described below. This assay is known in the art for anakinra. See also, e.g., PCT Publication No. WO 2004/022718.

All dilutions described below for this assay in Example 4 were done in assay media, which contained 1% FBS, 1% penicillin/streptomycin and 1% L-glutamine in DMEM. Ten thousand primary human chondrocytes (Cell Applications, Inc.; Cat. # 402-05, Lot # 1266) were aliquoted to each well of a 96-well flat-bottom plate (FALCON) in a final volume of 100 µl assay medium. The cells were incubated in a 37° C., 5% $CO_2$ incubator for four hours to recover. The test protein stock solutions, which included IL-1ra wild-type protein (stock concentration=1, mg/ml), IL-1ra K93A mutant protein (stock concentration=1.94 mg/ml), IL-1ra K93A mutant protein conc. (stock concentration=120 mg/ml), and IL-1ra R97D mutant protein (stock concentration=0.7 mg/ml) were separately serially diluted to concentrations ranging from 40,000 pM to 0.1526 pM in assay media. Specifically, the concentrations were 40,000 pM, 10,000 pM, 2,500 pM, 625 pM, 156.25 pM, 39.0625 pM, 9.766 pM, 2.441 pM, 0.6104 pM, and 0.1526 pM (these concentrations are 4× the final concentrations, which were 10,000 pM, 2,500 pM, 625 pM, 156.25 pM, 39.0625 pM, 9.766 pM, 2.441 pM, 0.6104 pM, 0.1526 pM, and 0.0381 pM). Fifty µl of each of the diluted test proteins were added to separate wells of the 96-well plate and the plate was incubated at 37° C. in 5% $CO_2$ for 30 minutes. A maximum activity control, which contained assay media but no test protein, was also included. Fifty µl of 8 pM recombinant human IL-1β (Amgen Inc.) was added to the wells, resulting in a final concentration of IL-1β of 2 pM. The plate was then incubated overnight (16 hours) in a 37° C., 5% $CO_2$ incubator.

The supernatants were removed from the cell cultures and the IL-6 levels in the supernatants were determined using IL-6 MSD plates (Meso Scale Discovery) and a human IL-6 ELISA kit (Pierce Endogen, Cat. # EH2IL65). The inhibition of IL-1β activity resulting from competition for binding to IL-1RI by each of the test proteins was calculated as a percentage of the electrochemiluminescence (MSD) or absorbance (ELISA) of the maximum activity control (no test proteins added).

The inhibition response curve for each test protein in this experiment was plotted and the results are shown in FIG. 6. FIG. 6A shows the results of an MSD-based assay. FIG. 6B shows the results of an ELISA-based assay. Both assays revealed that IL-1ra K93A mutant protein and IL-1ra R97D mutant protein are each effective at downregulating the expression of IL-6 on the surface of chondrocyte cells.

The corresponding $IC_{50}$ values (the concentration of test protein which reduces the signal by 50%) were calculated from the data in FIG. 6 using GraphPad PRISM software. The $IC_{50}$ for each of the IL-1ra wild-type and mutant proteins is shown below in Table 1.

TABLE 1

| | IL-1ra (1 mg/ml) | IL-1ra K93A (1.94 mg/m) | IL-1ra K93A (120 mg/ml) | IL-1ra R97D (0.7 mg/ml) |
|---|---|---|---|---|
| | MSD | | | |
| IC50 | 44.51 | 8.52 | 15.87 | 69.83 |
| | ELISA | | | |
| IC50 | 34.4 | 6.853 | 16.13 | 32.16 |

Example 5

Size-Exclusion Chromatography of IL-1ra Wild-Type and Mutant Proteins

Figure 7:
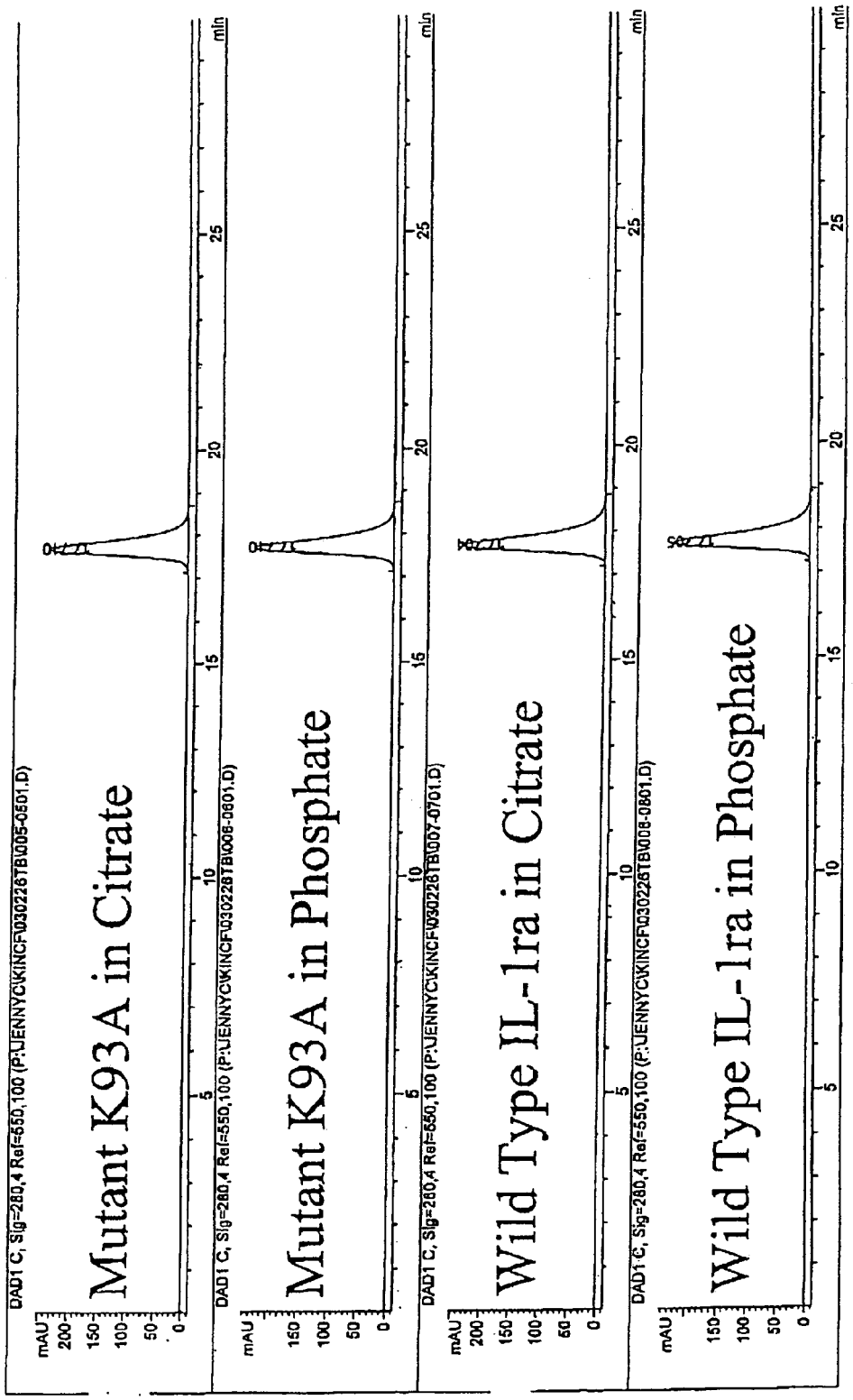
FIG. 7 shows the size-exclusion chromatography of IL-1ra K93A mutant protein and IL-1ra wild-type protein in either CSE or PSE discussed in Example 5.

Size-exclusion chromatography (SEC-HPLC) of each of IL-1ra wild-type protein and IL-1ra K93A mutant protein in PSE or CSE was performed at room temperature using a Toso Bioscience column (TSK-Gel G3000WXL, 5µ, 7.8×300 mm) on an HP1100 HPLC system. Isocratic elution was performed using CSE as the running buffer and an estimated sample load of 1 mg. As shown in FIG. 7, IL-1ra wild-type protein and IL-1 K93A mutant protein showed similar elution profiles in both PSE and CSE.

What is claimed is:

1. A method of reducing aggregation of an aggregating interleukin-1 receptor antagonist (IL-1ra) comprising making a variant of an IL-1ra comprising the amino acid sequence set forth in SEQ ID NO: 3,
   wherein the variant comprises an amino acid sequence that is at least 95% identical to the amino acid sequence set forth in SEQ ID NO: 3;
   wherein:
   a) the variant has an amino acid that does not have a charge at the position corresponding to Lysine-93 of SEQ ID NO: 3;
   b) the variant has an amino acid that does not have a charge at the position corresponding to Arginine-97 of SEQ ID NO: 3; or
   c) the variant has an amino acid that does not have a charge at the position corresponding to Lysine-93 of SEQ ID NO: 3 and an amino acid that does not have a charge at the position corresponding to Arginine-97 of SEQ ID NO: 3; and
   wherein if the variant has an arginine at the position corresponding to Arginine-97 of SEQ ID NO: 3, the variant does not have a threonine or a histidine at the position corresponding to Lysine-93 of SEQ ID NO: 3;
   thereby producing an IL-1ra having reduced aggregation.

2. The method of claim 1, wherein the variant has an amino acid selected from alanine, glycine, glutamine, asparagine, serine, threonine, and tyrosine at the position corresponding to Lysine-93 of SEQ ID NO: 3.

3. The method of claim 2, wherein the variant has an amino acid selected from alanine and glycine at the position corresponding to Lysine-93 of SEQ ID NO: 3.

4. The method of claim 1, comprising making a variant of an IL-1ra comprising SEQ ID NO: 3 with a methionine at the N-terminus, wherein the variant comprises an amino acid sequence that is at least 95% identical to SEQ ID NO: 3 with a methionine at the N-terminus.

5. The method of claim 1, wherein the variant comprises SEQ ID NO: 3 with a methionine at the N-terminus and has an alanine at the position corresponding to Lysine-93 of SEQ ID NO: 3.

6. The method of claim 1, wherein the variant has an amino acid that does not have a charge at the position corresponding to Arginine-97 of SEQ ID NO: 3.

7. The method of claim 1, wherein the variant has an amino acid selected from alanine, glycine, glutamine, asparagine, serine, threonine, and tyrosine at the position corresponding to Arginine-97 of SEQ ID NO: 3.

8. The method of claim 7, wherein the variant has an amino acid selected from alanine and glycine at the position corresponding to Arginine-97 of SEQ ID NO: 3.

9. The method of claim 1, further comprising incubating the IL-1ra having reduced aggregation with at least one accessory molecule, wherein at least one accessory molecule is selected from a sugar and a multiple-charge anion.

10. The method of claim 9, wherein at least one accessory molecule is a multiple-charge anion.

11. The method of claim 10, wherein said multiple-charge anion is 1 to 20 mM pyrophosphate.

12. The method of claim 10, wherein said multiple-charge anion is 1 to 20 mM citrate.

13. The method of claim 9, wherein at least one accessory molecule is a sugar.

14. The method of claim 13, wherein said sugar is glycerol, sucrose, or sorbitol.

15. The method of claim 13, wherein said sugar is at a concentration of from 1 to 3 percent.

16. The method of claim 1, further comprising incubating the IL-1ra having reduced aggregation with at least one accessory molecule, wherein at least one accessory molecule is selected from 6-(N-(7-nitrobenz-2-oxa-1,3-diazol-4-yl)amino)hexanoic acid (NBD-X), methyl acetyl phosphate (MAP), and citraconic anhydride.

17. A method of preparing an interleukin-1 receptor antagonist (IL-1ra) drug formulation comprising making a variant of an IL-1ra comprising the amino acid seguence set forth in SEQ ID NO: 3,
wherein the variant comprises an amino acid seguence that is at least 95% identical to the amino acid sequence set forth in SEQ ID NO: 3;
wherein:
a) the variant has an amino acid that does not have a charge at the position corresponding to Lysine-93 of SEQ ID NO: 3;
b) the variant has an amino acid that does not have a charge at the position corresponding to Arginine-97 of SEQ ID NO: 3; or
c) the variant has an amino acid that does not have a charge at the position corresponding to Lysine-93 of SEQ ID NO: 3 and an amino acid that does not have a charge at the position corresponding to Arginine-97 of SEQ ID NO: 3 and
wherein if the variant has an arginine at the position corresponding to Arginine-97 of SEQ ID NO: 3, the variant does not have a threonine or a histidine at the position corresponding to Lysine-93 of SEQ ID NO: 3;
thereby producing a drug formulation comprising an IL-1ra having reduced aggregation.

18. The method of claim 17, wherein the variant has an amino acid selected from alanine, glycine, glutamine, asparagine, serine, threonine, and tyrosine at the position corresponding to Lysine-93 of SEQ ID NO: 3.

19. The method of claim 18, wherein the variant has an amino acid selected from alanine and glycine at the position corresponding to Lysine-93 of SEQ ID NO: 3.

20. The method of claim 19, comprising making a variant of an IL-1ra comprising SEQ ID NO: 3 with a methionine at the N-terminus, wherein the variant comprises an amino acid sequence that is at least 95% identical to SEQ ID NO: 3 with a methionine at the N-terminus.

21. The method of claim 17, wherein the variant comprises SEQ ID NO: 3 with a methionine at the N-terminus and has an alanine at the position corresponding to Lysine-93 of SEQ ID NO: 3.

22. The method of claim 17, wherein the variant has an amino acid that does not have a charge at the position corresponding to Arginine-97 of SEQ ID NO: 3.

23. The method of claim 17, wherein the variant has an amino acid selected from alanine, glycine, glutamine, asparagine, serine, threonine, and tyrosine at the position corresponding to Arginine-97 of SEQ ID NO: 3.

24. The method of claim 23, wherein the variant has an amino acid selected from alanine and glycine at the position corresponding to Arginine-97 of SEQ ID NO: 3.

25. The method of claim 17, further comprising incubating the IL-1ra having reduced aggregation with at least one accessory molecule, wherein at least one accessory molecule is selected from a sugar and a multiple-charge anion.

26. The method of claim 25, wherein at least one accessory molecule is a multiple-charge anion.

27. The method of claim 26, wherein said multiple-charge anion is 1 to 20 mM pyrophosphate.

28. The method of claim 26, wherein said multiple-charge anion is 1 to 20 mM citrate.

29. The method of claim 25, wherein at least one accessory molecule is a sugar.

30. The method of claim 29, wherein said sugar is glycerol, sucrose, or sorbitol.

31. The method of claim 29, wherein said sugar is at a concentration of from 1 to 3 percent.

32. The method of claim 17, further comprising incubating the IL-1ra having reduced aggregation with at least one accessory molecule, wherein at least one accessory molecule is selected from 6-(N-(7-nitrobenz-2-oxa-1,3-diazol-4-yl)amino)hexanoic acid (NBD-X), methyl acetyl phosphate (MAP), and citraconic anhydride.

33. An isolated protein having the amino acid sequence shown in SEQ ID NO: 12, wherein $X_{aa}$ at position 94 is an amino acid that does not have a charge, and wherein $X_{aa}$ at position 94 is not a threonine or a histidine.

34. The protein of claim 33, wherein $X_{aa}$ at position 94 is an amino acid selected from alanine, glycine, glutamine, asparagine, serine, and tyrosine.

35. The protein of claim 34, wherein $X_{aa}$ at position 94 is an amino acid selected from alanine and glycine.

36. The protein of claim 33 produced in *E. coli*.

37. An isolated protein having the amino acid sequence shown in SEQ ID NO: 12, wherein $X_{aa}$ at position 98 is an amino acid that does not have a charge.

38. The protein of claim 37, wherein $X_{aa}$ at position 98 is an amino acid selected from alanine, glycine, glutamine, asparagine, serine, threonine, and tyrosine.

39. The protein of claim 38, wherein $X_{aa}$ at position 98 is an amino acid selected from alanine and glycine.

40. The protein of claim 37 produced in *E. coli*.

* * * * *

UNITED STATES PATENT AND TRADEMARK OFFICE
CERTIFICATE OF CORRECTION

PATENT NO.      : 7,619,066 B2                                                    Page 1 of 1
APPLICATION NO. : 11/097453
DATED           : November 17, 2009
INVENTOR(S)     : Raibekas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this

Twenty-sixth Day of October, 2010

David J. Kappos
*Director of the United States Patent and Trademark Office*

SEQUENCE LISTING

<160> NUMBER OF SEQ ID NOS: 13

<210> SEQ ID NO 1
<211> LENGTH: 600
<212> TYPE: DNA
<213> ORGANISM: Homo sapiens

<400> SEQUENCE: 1

```
gaattccggg ctgcagtcac agaatggaaa tctgcagagg cctccgcagt cacctaatca      60
ctctcctcct cttcctgttc cattcagaga cgatctgccg accctctggg agaaaatcca     120
gcaagatgca agccttcaga atctgggatg ttaaccagaa gaccttctat ctgaggaaca     180
accaactagt tgctggatac ttgcaaggac caaatgtcaa tttagaagaa aagatagatg     240
tggtaccat tgagcctcat gctctgttct tgggaatcca tggagggaag atgtgcctgt      300
cctgtgtcaa gtctggtgat gagaccagac tccagctgga ggcagttaac atcactgacc     360
tgagcgagaa cagaaagcag acaagcgct tcgccttcat ccgctcagac agtggcccca     420
ccaccagttt tgagtctgcc gcctgccccg gttggttcct ctgcacagcg atggaagctg     480
accagcccgt cagcctcacc aatatgcctg acgaaggcgt catggtcacc aaattctact     540
tccaggagga cgagtagtac tgcccaggcc tgctgttcca ttcttgcatg gcaaggactg     600
```

<210> SEQ ID NO 2
<211> LENGTH: 177
<212> TYPE: PRT
<213> ORGANISM: Homo sapiens

<400> SEQUENCE: 2

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110
```

```
Leu Ser Glu Asn Arg Lys Gln Asp Lys Arg Phe Ala Phe Ile Arg Ser
        115                 120                 125
Asp Ser Gly Pro Thr Thr Ser Phe Glu Ser Ala Ala Cys Pro Gly Trp
    130                 135                 140
Phe Leu Cys Thr Ala Met Glu Ala Asp Gln Pro Val Ser Leu Thr Asn
145                 150                 155                 160
Met Pro Asp Glu Gly Val Met Val Thr Lys Phe Tyr Phe Gln Glu Asp
                165                 170                 175
Glu

<210> SEQ ID NO 3
<211> LENGTH: 152
<212> TYPE: PRT
<213> ORGANISM: Homo sapiens

<400> SEQUENCE: 3

Arg Pro Ser Gly Arg Lys Ser Ser Lys Met Gln Ala Phe Arg Ile Trp
1               5                   10                  15
Asp Val Asn Gln Lys Thr Phe Tyr Leu Arg Asn Asn Gln Leu Val Ala
            20                  25                  30
Gly Tyr Leu Gln Gly Pro Asn Val Asn Leu Glu Glu Lys Ile Asp Val
        35                  40                  45
Val Pro Ile Glu Pro His Ala Leu Phe Leu Gly Ile His Gly Gly Lys
    50                  55                  60
Met Cys Leu Ser Cys Val Lys Ser Gly Asp Glu Thr Arg Leu Gln Leu
65                  70                  75                  80
Glu Ala Val Asn Ile Thr Asp Leu Ser Glu Asn Arg Lys Gln Asp Lys
                85                  90                  95
Arg Phe Ala Phe Ile Arg Ser Asp Ser Gly Pro Thr Thr Ser Phe Glu
            100                 105                 110
Ser Ala Ala Cys Pro Gly Trp Phe Leu Cys Thr Ala Met Glu Ala Asp
        115                 120                 125
Gln Pro Val Ser Leu Thr Asn Met Pro Asp Glu Gly Val Met Val Thr
    130                 135                 140
Lys Phe Tyr Phe Gln Glu Asp Glu
145                 150

<210> SEQ ID NO 4
<211> LENGTH: 475
<212> TYPE: DNA
<213> ORGANISM: Homo sapiens

<400> SEQUENCE: 4
catatgcgac cgtccggccg taagagctcc aaaatgcagg ctttccgtat ctgggacgtt    60
aaccagaaaa ccttctacct gcgcaacaac cagctggttg ctggctacct gcagggtccg   120
aacgttaacc tggaagaaaa aatcgacgtt gtaccgatcg aaccgcacgc tctgttcctg   180
ggtatccacg gtggtaaaat gtgcctgagc tgcgtgaaat ctggtgacga aactcgtctg   240
cagctggaag cagttaacat cactgacctg agcgaaaacc gcaaacagga caaacgtttc   300
gcattcatcc gctctgacag cggcccgacc accagcttcg aatctgctgc ttgcccgggt   360
tggttcctgt gcactgctat ggaagctgac cagccggtaa gcctgaccaa catgccggac   420
gaaggcgtga tggtaaccaa attctacttc caggaagacg aataatggga agctt         475

<210> SEQ ID NO 5
```

<211> LENGTH: 153
<212> TYPE: PRT
<213> ORGANISM: Homo sapiens

<400> SEQUENCE: 5

```
Met Arg Pro Ser Gly Arg Lys Ser Ser Lys Met Gln Ala Phe Arg Ile
 1               5                  10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```

<210> SEQ ID NO 6
<211> LENGTH: 25
<212> TYPE: DNA
<213> ORGANISM: Artificial
<220> FEATURE:
<223> OTHER INFORMATION: Oligonucleotide primer

<400> SEQUENCE: 6
cgtacaggtt tacgcaagaa aatgg                                         25

<210> SEQ ID NO 7
<211> LENGTH: 30
<212> TYPE: DNA
<213> ORGANISM: Artificial
<220> FEATURE:
<223> OTHER INFORMATION: Oligonucleotide primer

<400> SEQUENCE: 7
cgtttgtcct gagcgcggtt ttcgctcagg                                    30

<210> SEQ ID NO 8
<211> LENGTH: 33
<212> TYPE: DNA
<213> ORGANISM: Artificial
<220> FEATURE:
<223> OTHER INFORMATION: Oligonucleotide primer

<400> SEQUENCE: 8
gagcgaaaac cgcgctcagg acaaacgttt cgc                                33

<210> SEQ ID NO 9
<211> LENGTH: 18
<212> TYPE: DNA
<213> ORGANISM: Artificial
<220> FEATURE:
<223> OTHER INFORMATION: Oligonucleotide primer

```
<400> SEQUENCE: 9
ctagttattg ctcagcgg                                                    18

<210> SEQ ID NO 10
<211> LENGTH: 29
<212> TYPE: DNA
<213> ORGANISM: Artificial
<220> FEATURE:
<223> OTHER INFORMATION: Oligonucleotide primer

<400> SEQUENCE: 10
gaatgcgagt cgtttgtcct gtttgcggt                                        29

<210> SEQ ID NO 11
<211> LENGTH: 32
<212> TYPE: DNA
<213> ORGANISM: Artificial
<220> FEATURE:
<223> OTHER INFORMATION: Oligonucleotide primer

<400> SEQUENCE: 11
aaacaggaca aagacttcgc attcatccgc tc                                    32

<210> SEQ ID NO 12
<211> LENGTH: 153
<212> TYPE: PRT
<213> ORGANISM: Artificial
<220> FEATURE:
<223> OTHER INFORMATION: Hypothetical IL-1ra showing variable amino
      acids
<220> FEATURE:
<221> NAME/KEY: Xaa
<222> LOCATION: (17)..(17)
<223> OTHER INFORMATION: Xaa is any amino acid
<220> FEATURE:
<221> NAME/KEY: Xaa
<222> LOCATION: (35)..(35)
<223> OTHER INFORMATION: Xaa is any amino acid
<220> FEATURE:
<221> NAME/KEY: Xaa
<222> LOCATION: (94)..(94)
<223> OTHER INFORMATION: Xaa is any amino acid
<220> FEATURE:
<221> NAME/KEY: Xaa
<222> LOCATION: (98)..(98)
<223> OTHER INFORMATION: Xaa is any amino acid

<400> SEQUENCE: 12
```

Met Arg Pro Ser Gly Arg Lys Ser Ser Lys Met Gln Ala Phe Arg Ile
1               5                   10                  15

Xaa Asp Val Asn Gln Lys Thr Phe Tyr Leu Arg Asn Asn Gln Leu Val
            20                  25                  30

Ala Gly Xaa Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Xaa Gln Asp
                85                  90                  95

Lys Xaa Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

-continued

```
Asp Gln Pro Val Ser Leu Thr Asn Met Pro Glu Gly Val Met Val
        130                 135                 140

Thr Lys Phe Tyr Phe Gln Glu Asp Glu
145                 150

<210> SEQ ID NO 13
<211> LENGTH: 159
<212> TYPE: PRT
<213> ORGANISM: Homo sapiens

<400> SEQUENCE: 13

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
            85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
            115                 120                 125

Cys Thr Ala Met Glu Ala Asp Gln Pro Val Ser Leu Thr Asn Met Pro
        130                 135                 140

Asp Glu Gly Val Met Val Thr Lys Phe Tyr Phe Gln Glu Asp Glu
145                 150                 155
```